United States Patent
Tsai et al.

(10) Patent No.: US 10,576,262 B2
(45) Date of Patent: Mar. 3, 2020

(54) SPRING-LOADED BAG CONNECTOR

(71) Applicant: ConvaTec Technologies Inc., Las Vegas, NV (US)

(72) Inventors: Mingliang Lawrence Tsai, Holmdel, NJ (US); Tinh Nguyen Demary, Milltown, NJ (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 453 days.

(21) Appl. No.: 15/158,426

(22) Filed: May 18, 2016

(65) Prior Publication Data

US 2016/0339227 A1 Nov. 24, 2016

Related U.S. Application Data

(60) Provisional application No. 62/163,240, filed on May 18, 2015.

(51) Int. Cl.
*A61M 39/22* (2006.01)
*A61F 5/451* (2006.01)
(Continued)

(52) U.S. Cl.
CPC ............ *A61M 39/22* (2013.01); *A61F 5/451* (2013.01); *A61M 39/1011* (2013.01);
(Continued)

(58) Field of Classification Search
CPC .. A61M 39/1011; A61M 39/22; A61M 39/26; A61M 2039/1027;
(Continued)

(56) References Cited

U.S. PATENT DOCUMENTS

| 851,530 A | 4/1907 | Edward |
|---|---|---|
| 2,254,997 A | 9/1941 | Fisher |

(Continued)

FOREIGN PATENT DOCUMENTS

| CN | 105407961 A | 3/2016 |
|---|---|---|
| EP | 1514572 A2 | 3/2005 |

(Continued)

OTHER PUBLICATIONS

European Patent Application No. 12849279.0 Communication dated Mar. 23, 2016.

(Continued)

*Primary Examiner* — Benjamin J Klein
(74) *Attorney, Agent, or Firm* — Taft Stettinius & Hollister LLP

(57) ABSTRACT

A spring-loaded bag connector having a spring-loaded valve and a housing comprising a fluid inlet portion and a fluid outlet portion. The spring-loaded bag connector is configured to connect with a fluid collection bag to generate a self-closing collection bag. Additionally, the spring-loaded bag connector is configured to couple with a second coupling element, such as a coupling connector, to facilitate the drainage and collection of waste to a fluid collection bag. Uncoupling of the bag connector and the second coupling element results in minimal fluid contamination on the outer surfaces of the bag connector system. The bag connector systems provided herein are included in medical appliances for body waste management.

16 Claims, 9 Drawing Sheets

(51) Int. Cl.
*A61M 39/26* (2006.01)
*A61M 39/10* (2006.01)

(52) U.S. Cl.
CPC ..... *A61M 39/26* (2013.01); *A61M 2039/1027* (2013.01); *A61M 2039/226* (2013.01); *A61M 2207/00* (2013.01)

(58) Field of Classification Search
CPC ......... A61M 2039/226; A61M 2207/00; A61F 5/451; A61J 1/10; A61J 1/14–1481
See application file for complete search history.

(56) References Cited

U.S. PATENT DOCUMENTS

| | | | |
|---|---|---|---|
| 3,127,148 | A | 3/1964 | Collar |
| 3,211,150 | A | 10/1965 | Foderick |
| 3,446,245 | A | 5/1969 | Clifford, Jr. |
| 3,721,726 | A | 3/1973 | Schwartzman |
| 3,777,757 | A | 12/1973 | Gray et al. |
| 4,116,201 | A | 9/1978 | Shah |
| 4,178,938 | A | 12/1979 | Au |
| 4,280,498 | A | 7/1981 | Jensen |
| 4,431,019 | A | 2/1984 | Kopp et al. |
| 4,541,457 | A | 9/1985 | Blenkush |
| 4,629,159 | A | 12/1986 | Wellenstam |
| 4,948,092 | A | 8/1990 | Kasper et al. |
| 4,955,879 | A | 9/1990 | Mervine |
| 5,350,364 | A | 9/1994 | Stephens et al. |
| 5,454,784 | A | 10/1995 | Atkinson et al. |
| 5,496,300 | A | 3/1996 | Hirsch et al. |
| 5,609,195 | A | 3/1997 | Stricklin et al. |
| 5,628,726 | A * | 5/1997 | Cotter .................. A61M 39/14 137/614.04 |
| 5,709,244 | A | 1/1998 | Patriquin et al. |
| 5,957,151 | A | 9/1999 | Dalcourt et al. |
| 6,045,542 | A | 4/2000 | Cawood |
| 6,050,973 | A | 4/2000 | Duffy |
| 6,146,374 | A | 11/2000 | Erskine et al. |
| 6,655,656 | B2 | 12/2003 | Maldavs |
| 7,261,125 | B1 | 8/2007 | Lien et al. |
| 7,727,188 | B2 | 6/2010 | Machado et al. |
| 8,012,132 | B2 | 9/2011 | Lum et al. |
| 8,016,816 | B2 | 9/2011 | Gregory |
| 8,052,671 | B2 | 11/2011 | Christensen et al. |
| 8,888,739 | B2 | 11/2014 | Gregory et al. |
| 9,072,875 | B2 | 7/2015 | Jin et al. |
| 9,623,201 | B2 | 4/2017 | Gregory et al. |
| 9,669,205 | B2 | 6/2017 | Jin et al. |
| 9,808,606 | B2 | 11/2017 | Jin et al. |
| 2003/0079752 | A1 | 5/2003 | Hart et al. |
| 2003/0106610 | A1 | 6/2003 | Roos et al. |
| 2003/0221728 | A1 | 12/2003 | Enerson |
| 2003/0229259 | A1 | 12/2003 | Waksman et al. |
| 2004/0010238 | A1 | 1/2004 | Manera et al. |
| 2004/0039374 | A1 | 2/2004 | Tighe et al. |
| 2004/0158197 | A1 | 8/2004 | Bellhouse et al. |
| 2004/0176703 | A1 | 9/2004 | Christensen et al. |
| 2005/0054996 | A1 | 3/2005 | Gregory |
| 2005/0082828 | A1 | 4/2005 | Wicks et al. |
| 2005/0101939 | A1 | 5/2005 | Mitchell |
| 2005/0124932 | A1 | 6/2005 | Foster et al. |
| 2005/0256460 | A1 | 11/2005 | Rome et al. |
| 2005/0273083 | A1 | 12/2005 | Lebel et al. |
| 2007/0123832 | A1 | 5/2007 | Cline et al. |
| 2007/0142700 | A1 * | 6/2007 | Fogarty .................. A61F 2/26 600/40 |
| 2007/0149922 | A1 | 6/2007 | Schneider et al. |
| 2007/0215221 | A1 * | 9/2007 | Lien .................. F16L 37/098 137/614.04 |
| 2008/0009794 | A1 | 1/2008 | Bagaoisan et al. |
| 2008/0103463 | A1 | 5/2008 | Tsai et al. |
| 2008/0114316 | A1 | 5/2008 | Christensen et al. |
| 2008/0147012 | A1 | 6/2008 | Rome |
| 2008/0175719 | A1 | 7/2008 | Tracey et al. |
| 2009/0163892 | A1 | 6/2009 | McMichael et al. |
| 2010/0191192 | A1 | 7/2010 | Prasad et al. |
| 2010/0217189 | A1 | 8/2010 | Pepper |
| 2010/0274189 | A1 | 10/2010 | Kurth et al. |
| 2011/0295236 | A1 | 12/2011 | Gregory |
| 2013/0030387 | A1 | 1/2013 | Williams et al. |
| 2013/0071170 | A1 | 3/2013 | Mehus et al. |
| 2014/0052063 | A1 | 2/2014 | Gregory et al. |
| 2014/0107572 | A1 | 4/2014 | Jin et al. |
| 2014/0276497 | A1 * | 9/2014 | Robinson ............ A61M 1/0056 604/321 |
| 2015/0051542 | A1 | 2/2015 | Gregory et al. |
| 2015/0059901 | A1 * | 3/2015 | Jin .................. A61M 39/1011 137/798 |
| 2016/0339227 | A1 | 11/2016 | Tsai et al. |
| 2017/0173310 | A1 | 6/2017 | Gregory et al. |
| 2017/0252549 | A1 | 9/2017 | Jin et al. |
| 2017/0259046 | A9 | 9/2017 | Jin et al. |
| 2018/0229013 | A1 | 8/2018 | Tsai |

FOREIGN PATENT DOCUMENTS

| | | |
|---|---|---|
| EP | 3027266 A1 | 6/2016 |
| EP | 3297585 A1 | 3/2018 |
| JP | S52158920 U | 12/1977 |
| JP | S58-501012 A | 6/1983 |
| JP | S61192991 A | 8/1986 |
| JP | H0629590 Y2 | 8/1994 |
| JP | H09327519 A | 12/1997 |
| JP | H09512892 A | 12/1997 |
| JP | 2003502588 A | 1/2003 |
| JP | 2007523296 A | 8/2007 |
| JP | 2008117545 A | 5/2008 |
| WO | WO-8300070 A1 | 1/1983 |
| WO | WO-9530856 A1 | 11/1995 |
| WO | WO-2004045704 A2 | 6/2004 |
| WO | WO-2006/043883 | 4/2006 |
| WO | WO-2011100187 A1 | 8/2011 |
| WO | WO-2013074763 A1 | 5/2013 |
| WO | WO-2013109293 | 7/2013 |
| WO | WO-2015017646 A1 | 2/2015 |
| WO | WO-2016187350 A1 | 11/2016 |
| WO | WO-2017075226 A1 | 5/2017 |

OTHER PUBLICATIONS

PCTUS2014/049115 International Preliminary Report on Patentability dated Feb. 11, 2016.
PCT/US2012/025420 International Preliminary Report on Patentability dated Aug. 21, 2013.
PCT/US2012/025420 International Search Report and Written Opinion dated Jun. 6, 2012.
PCT/US2012/065239 International Preliminary Report on Patentability dated May 20, 2014.
PCT/US2012/065239 International Search Report completed Mar. 8, 2013.
PCT/US2012/065239 Written Opinion completed Mar. 8, 2013.
PCT/US2014/049115 International Search Report completed Oct. 28, 2014.
PCT/US2014/049115 Written Opinion completed Oct. 28, 2014.
ROC (Taiwan) Patent Application No. 101142959 Office Action dated Mar. 21, 2016.
U.S. Appl. No. 13/877,890 Office Action dated Mar. 27, 2014.
U.S. Appl. No. 14/000,384 Office Action dated Sep. 11, 2014.
U.S. Appl. No. 14/341,647 Office Action dated May 5, 2016.
U.S. Appl. No. 14/449,035 Office Action dated Feb. 12, 2016.
U.S. Appl. No. 14/745,312 Office Action dated Feb. 17, 2016.
Australia Patent Application No. 2017200016 Examination Report No. 1 dated Nov. 14, 2017.
Japanese Patent Application No. 2014-542455 Office Action dated Nov. 14, 2017.
PCT/US2016/033147 International Preliminary Report on Patentability dated Nov. 30, 2017.
U.S. Appl. No. 15/495,712 Office Action dated Jan. 5, 2018.

(56) References Cited

OTHER PUBLICATIONS

Australian Patent Application No. 2012340411 Examiner's First Report dated Jul. 14, 2016.
Chinese Patent Application No. 201280067212.0 Second Office Action dated Jul. 12, 2016.
Chinese Patent Application No. 201280067212.0 Third Office Action dated Feb. 27, 2017.
European Patent Application No. 12849279.0 Communication dated Aug. 18, 2016.
European Patent Application No. 14832568.1 Supplementary European Search Report dated Feb. 15, 2017.
Japanese Patent Application No. 2014-542455 Office Action dated Dec. 6, 2016.
Mexican Patent Application No. MX/a/2014/005934 Office Action dated Jul. 14, 2016.
New Zealand Patent Application No. 727366 First Examiner's Report dated Jan. 17, 2017.
PCT/US2016/033147 International Search Report and Written Opinion dated Aug. 16, 2016.
Russian Patent Application No. 2014124144 Office Action dated Nov. 14, 2016.
Taiwan Patent Application No. 105113600 Office Action dated Jan. 16, 2017.
U.S. Appl. No. 14/449,035 Office Action dated Sep. 14, 2016.
U.S. Appl. No. 15/495,712 Restriction Requirement dated Oct. 6, 2017.
Japanese Patent Application No. 2016-531895 Office Action dated Jun. 11, 2019.
PCT/US2016/059132 International Preliminary Report on Patentability dated May 1, 2018.
PCT/US2016/059132 International Search Report and Written Opinion dated Jan. 6, 2017.
U.S. Appl. No. 15/448,274 Restriction Requirement dated Nov. 15, 2018.
U.S. Appl. No. 15/495,712 Advisory Action dated Dec. 13, 2018.
U.S. Appl. No. 15/495,712 Office Action dated Jan. 24, 2019.
U.S. Appl. No. 15/495,712 Office Action dated Sep. 5, 2018.

* cited by examiner

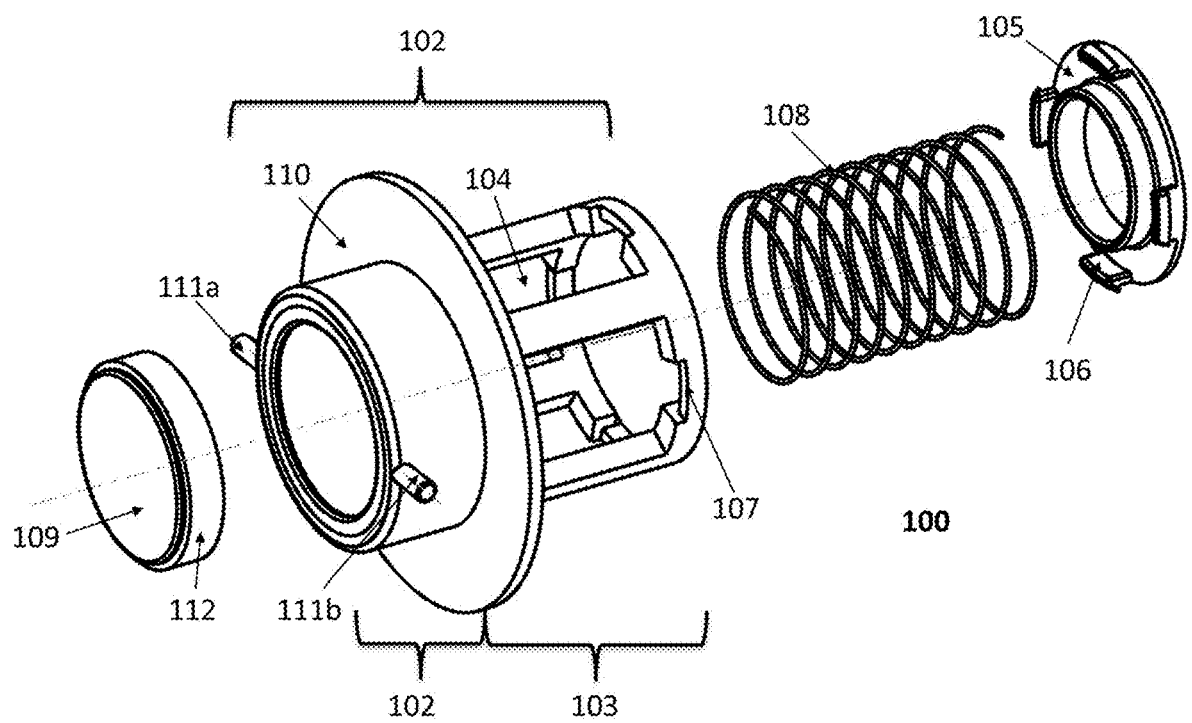

FIG 4C
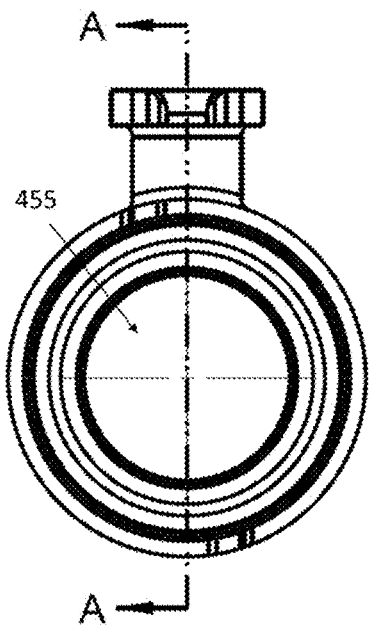
FG 4D
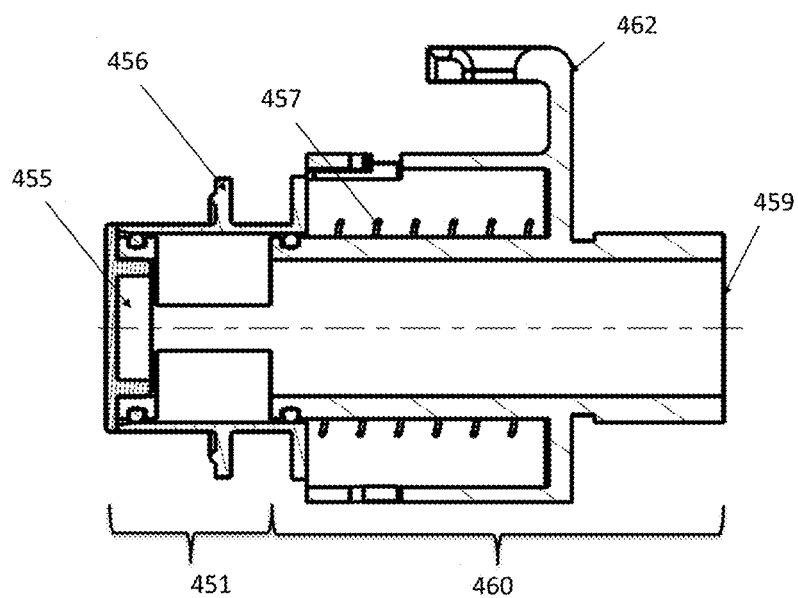

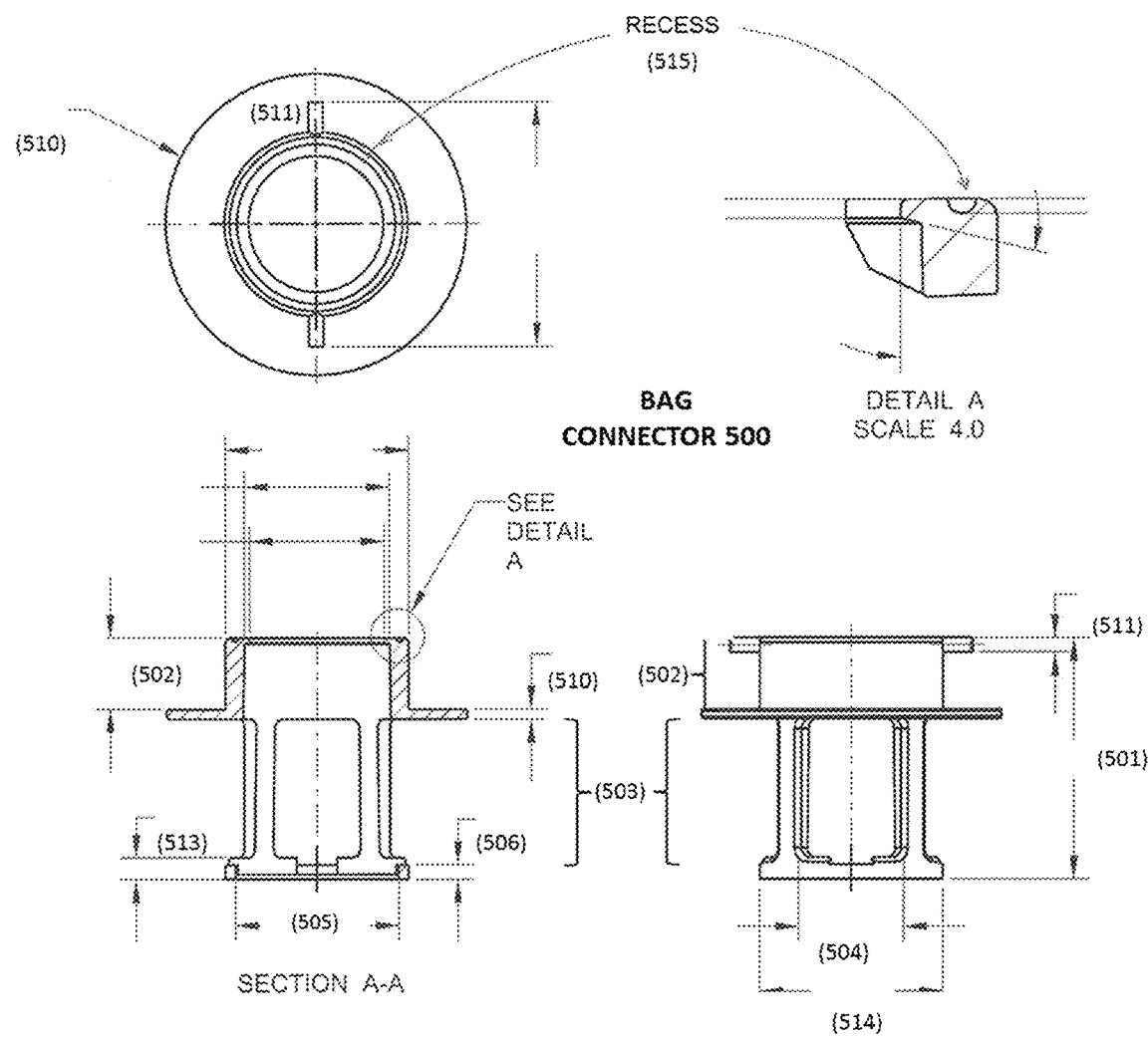

SPRING-LOADED BAG CONNECTOR

CROSS-REFERENCE

This application claims the benefit of U.S. Provisional Application No. 62/163,240 filed May 18, 2015, which application is incorporated herein by reference.

BACKGROUND OF THE INVENTION

Bag connector systems are used in a wide range of medical appliances to connect medical grade tubing to an external fluid collection bag. Such fluid is liquid or semi-liquid in nature, for example, containing particulates or other solid material. Collected fluid includes waste fluid, including liquid or semi-liquid feces, urine or other bodily fluid. It is desirable to design a bag connector system that is easy to use, manipulatable, and hygienic.

SUMMARY OF THE INVENTION

In one aspect, provided herein is a bag connector device for use in a bag connector system. In some embodiments, a bag connector system comprises a bag connector configured for connecting a fluid collection bag to a component of a medical device useful for facilitating the drainage and/or collection of fluid and/or matter. Exemplary medical devices include, without limitation, catheters, catheter adaptors, coupling connectors and medical grade tubing. In one aspect, provided herein is a bag connector comprising a housing having a fluid inlet portion and a fluid outlet portion. The bag connector is configured to allow the passage of fluid and/or matter from the fluid inlet portion to the fluid outlet portion through the interior of the housing. In some embodiments, the fluid outlet portion comprises one or more openings to allow fluid and/or matter to exit the interior of the fluid outlet portion of the housing. In some embodiments, the bag connector is configured to allow for the passage of fluid and/or matter from the interior of the fluid inlet portion to the exterior of the fluid outlet portion through the one or more openings.

In one aspect, the bag connector comprises a fixture for the attachment of a fluid collection bag to the housing. In some embodiments, the attachment fixture comprises a flange configured to attach to a fluid collection bag, for example, by using an adhesive (i.e., gluing), heat welding, or ultrasonic welding. Provided herein, in some embodiments, is a bag connector comprising a housing having a fluid inlet portion and a fluid outlet portion, wherein the housing is attached to a fluid collection bag. The fluid collection bag may be welded to the housing or removably attached. In some embodiments, the fluid outlet portion of the housing is positioned within the fluid collection bag. In some embodiments, the fluid inlet portion of the housing is positioned outside of the fluid collection bag. In another embodiment, provided herein is a self-closing collection bag comprising a fluid collection bag and a bag connector. In an exemplary embodiment, the bag connector is configured to allow for the passage of fluid and/or matter from the interior of the fluid inlet portion to the interior of the fluid collection bag through one or more openings of the fluid outlet portion of the bag connector.

In one aspect, the bag connector comprises an engaging element useful for coupling the bag connector to a second device, such as a catheter or a coupling connector comprising or configured for attachment to a catheter. In one aspect the second device comprises an engaging element configured for coupling to the bag connector. An engaging element includes, without limitation, one or more prongs for use in a twist-lock mechanism. The prongs for us in a twist-lock mechanism can reside either in the first coupling element or in the second coupling element. An engaging element also includes a rotating locking member configured to engage with the one or more prongs. Provided herein, in some embodiments, is a bag connector engaged with a second device, wherein the bag connector is a first coupling element and the second device is a second coupling element. In some embodiments, when the first and second elements are coupled, a system is created which allows for the controlled passage of fluid and/or matter from the second coupling element to the interior of the housing of the first coupling element, and subsequently through the fluid outlet portion openings of the first element. In some embodiments, the first and second elements are coupled, wherein the first element is attached to a fluid collection bag and the system allows for the controlled passage of fluid and/or matter from the second coupling element to the fluid collection bag through the first coupling element. In a further embodiment, the uncoupling of the first coupling element and the second coupling element prevents fluid from exiting the housing of the first coupling element, the housing of the second coupling element or the housings of both the first and second coupling elements. In some embodiments, the second coupling element is a spring-loaded coupling connector. In certain embodiments, the bag connector is configured to engage with a second coupling element, wherein the second coupling element is configured to further engage with a catheter. In one example, a second device coupled to the bag connector comprises a second coupling element and a catheter. In one example, the second coupling element is a catheter adaptor. As used herein, at least in some instances, a catheter is synonymous with a device comprising medical grade tubing configured to remove fluid from a subject.

In some embodiments, the bag connector further comprises a base configured to connect to the bottom of the housing at the fluid outlet portion. In some instances, the base is a component of the housing. In some instances, the base is removably attached to the housing. In other instances, the base is welded or glued to the housing.

In one aspect, disclosed herein is a bag connector comprising a) a housing having a fluid inlet portion and a fluid outlet portion and b) a spring-loaded valve. In an exemplary embodiment, the spring-loaded valve comprises a spring element and a moving door supported by the spring element. In some embodiments, the spring element and the moving door are positioned within the interior of the housing. In some embodiments, the bag connector comprises a base positioned at the bottom end of the housing at the fluid outlet portion. The base may be a component of either the housing or the spring-loaded valve. In some embodiments, the base provides a seat for the spring element of the spring-loaded valve. In some embodiments, the bag connector comprises an engaging element to engage with a second device, for example, a catheter or coupling connector. In some embodiments, coupling of the bag connector to a second device results in the compression of the spring-loaded valve and the bag connector has an open configuration. In another embodiment, uncoupling of the bag connector from the second device results in the decompression of the spring-loaded valve and the bag connector has a closed configuration. In a further embodiment, a bag connector in a closed configuration provides minimal fluid contamination. In another embodiment, the bag connector further comprises a fixture to connect the bag connector to a fluid collection bag. In some embodiments, the fixture is a flange. In some embodiments, the flange is welded or attached by adhesives to the collection bag. In some embodiments, the bag is constructed to form a three-dimensional shape since a portion of the bag connector is recessed into the inside of the bag. Such a three-dimensional shape of the collection bag can increase the bag capacity without any change in the footprint (i.e., length and width) of the collection bag. In some embodiments, the collection bag is thermoformed or blow-molded. In yet other embodiments the collection bag comprises pleats or folds. In still other embodiments, the collection bag is rigid or semi-rigid in structure.

In one aspect, provided herein is a spring-loaded bag connector comprising a) a housing having a fluid inlet portion and a fluid outlet portion, wherein the fluid outlet portion has a structure comprising one or more openings to allow for the exiting of fluid from the housing; and b) a spring-loaded valve to regulate the exiting of fluid from the housing; wherein compression of the spring-loaded valve results in an open configuration allowing fluid to exit through the openings of the housing; and wherein decompression of the spring-loaded valve results in a closed configuration restricting fluid from exiting the housing. In some embodiments, the spring-loaded valve is self-closing, minimizing fluid contamination on exterior surfaces of the bag connector. In some embodiments, the spring-loaded bag connector further comprising a fixture for attaching a fluid collection bag to the bag connector to generate a self-closing collection bag. In some embodiments, the one or more openings of the fluid outlet portion of the housing is enclosed within the fluid collection bag. In some embodiments, the fixture is a flange.

In some embodiments, the spring-loaded valve of a spring-loaded bag connector is positioned within the housing of the bag connector. In some embodiments, a spring-loaded bag connector further comprises a base connected to the housing at the fluid outlet portion. In some embodiments, a spring-loaded valve comprises a spring element. A spring-loaded valve, in some embodiments, comprises a spring element and a moving door, wherein the moving door is supported by the spring element.

In some embodiments, a spring-loaded bag connector is a first coupling element in a system, wherein the spring-loaded bag connector is configured to couple to a second coupling element in the system. In some embodiments, the spring-loaded bag connector comprises an engaging element for coupling the spring-loaded bag connector to a second coupling element. In some embodiments, the second coupling element is a coupling connector. In some embodiments, the second coupling element is a catheter. In other embodiments, the second coupling element connects to a catheter. In another embodiment, coupling of the spring-loaded bag connector to a second coupling element results in the compression of the spring-loaded valve. In a further embodiment, uncoupling of the spring-loaded bag connector to the second coupling element results in the decompression of the spring-loaded valve. In some embodiments, the engaging element of the spring-loaded bag connector comprises one or more prongs. In another embodiment, the spring-loaded bag connector and the second coupling element are maintained in a coupled state by a twist-lock in mechanism. In some embodiments, the second coupling element is a spring-loaded coupling connector. In further embodiments, coupling of the spring-loaded bag connector to the spring-loaded coupling connector results in the compression of a spring-loaded valve of the spring-loaded coupling connector. In additional embodiments, uncoupling of the spring-loaded bag connector to the spring-loaded coupling connector results in the decompression of the spring-loaded valve of the spring-loaded coupling connector.

In one aspect, disclosed herein are bag connector systems comprising a) a bag connector comprising a housing having a fluid inlet portion and a fluid outlet port, the bag connector further comprising a spring-loaded valve to prevent fluid flow from exiting the fluid outlet port; b) and a second device comprising a fluid inlet end and a fluid outlet end; wherein the fluid outlet end of the second device is configured to displace the spring-loaded valve when inserted into the housing of the bag connector resulting in a coupled state; and wherein uncoupling of the bag connector and the second device results in minimal fluid contamination of exterior surfaces of the system. In some embodiments, the second device is a spring-loaded coupling connector comprising a second spring-loaded valve, wherein the fluid inlet portion of the bag connector is configured to displace the second spring-loaded valve when inserted into the housing of the spring-loaded coupling connector. In some embodiments, the bag connector comprises a fixture to attach a fluid collection bag to the housing. In some embodiments, the bag connector comprises or is attached to a fluid collection bag. In some embodiments, the bag connector comprises or is attached to a fluid collection bag, wherein the fluid outlet portion of the housing is positioned within the fluid collection bag. In some embodiments, the exterior surfaces of the system comprises the exterior of the fluid inlet portion of the bag connector and the exterior of the fluid collection bag. In some embodiments, the exterior surfaces of the system comprises the exterior of the fluid inlet end and the exterior of the fluid collection bag. In some embodiments, the bag connector is a first coupling element of the bag connector system and the second device is a second coupling element of the bag connector system. In some embodiments, the second coupling element is a spring-loaded coupling connector.

In some embodiments, the first coupling element and the second coupling element are configured to engage in a coupled state by use of one or more engaging elements. In some embodiments, the coupling elements are maintained in a coupled state via a twist lock-in mechanism. In some embodiments, the second coupling element comprises a sliding cover positioned over the fluid outlet port. In some embodiments, the second coupling element further comprises at least one O-ring. In further embodiments, the bag connector and the second coupling element are maintained in a coupled state by the use of at least one cantilever snap, preferably a plurality of cantilever snaps, at the fluid inlet portion of the bag connector which forms a snap-fit with the sliding cover on the second coupling element.

In some embodiments, the spring-loaded valve is positioned within the housing of the bag connector. In some embodiments, the spring-loaded valve comprises a moving door connected to a spring. In further embodiments, the spring-loaded valve comprises a spring seat, a spring element, and a moving door. In still further embodiments, the spring-loaded valve is a poppet valve. 1. In some embodiments, when the bag connector is disconnected or uncoupled from the second coupling element, the bag connector is in a closed status, closing a drainage path with the second coupling element. In some embodiments, when connecting the bag connector with the second coupling element, the second coupling element pushes against the moving door in the bag connector until one or more openings on the fluid outlet portion of the bag connector is exposed, resulting in an open conformation. Upon opening by the second coupling element, the drainage path of the bag connector is opened, allowing for the passage of fluid and/matter from the interior of the housing to be released to the exterior of the fluid outlet portion. In some embodiments, opening by the second coupling element results in a drainage path on both the bag connector and the second coupling element to become open for drainage. For example, opening of the system by engagement of the bag connector with the second coupling element allows for the passage of fluid and/or matter from the second coupling element through the interior of the housing of the bag connector, to the outside of the fluid outlet portion of the housing. In exemplary embodiments, the fluid and/or matter is collected in a fluid collection bag, wherein the fluid collection bag encases the fluid outlet portion of the housing of the bag connector. In yet other embodiments, upon disconnection of the bag connector and the second coupling element, the spring element may push the moving door of the bag connector into position to close off the drainage path. In some embodiments, the material of the moving door is softer than the material of the housing. In yet other embodiments, the material of the moving door at the point where the moving door and housing meet is softer than the surrounding material. In still other embodiments, the hardness of the softer material is between Shore A 30 to Shore A 90. In some embodiments, the softer material is incorporated with a two-shot injection mold. In another embodiment, the bag connector further comprises an O-ring between the housing and moving door.

In one aspect, disclosed herein are spring-loaded bag connector systems comprising a) a first coupling element comprising a housing having a fluid inlet portion and a fluid outlet portion, wherein the fluid outlet portion has a structure comprising one or more openings to allow for the exiting of fluid from the housing, wherein the first coupling element further comprises a spring-loaded valve to prevent fluid from exiting the housing; and b) a second coupling element comprising a second housing having a fluid inlet end and a fluid outlet end, the fluid outlet end configured to displace the spring-loaded valve when inserted into the housing of the first coupling element to generate a coupled state. In some embodiments, the second coupling element is a spring-loaded coupling connector comprising a spring-loaded valve. In further embodiments, coupling of the spring-loaded bag connector to the spring-loaded coupling connector results in the compression of a spring-loaded valve of the spring-loaded coupling connector.

In another aspect, disclosed herein are medical appliances comprising a fluid storage bag and a bag connector system, the bag connector system comprising a bag connector comprising a housing having a fluid inlet portion and a fluid outlet port, the bag connector further comprising a spring-loaded valve to prevent fluid flow from exiting the fluid outlet port; and a second device comprising a housing having a fluid inlet end and a fluid outlet end, the fluid outlet end configured to displace the spring-loaded valve when inserted into the fluid inlet portion of the bag connector; and wherein the fluid outlet portion of the second device is enclosed within a fluid storage container; and wherein uncoupling of the first coupling element and the second coupling element results in minimal fluid contamination on the outer surfaces of the medical appliance. In yet another aspect, disclosed herein are medical appliances comprising a fluid collection container and a bag connector system, the bag connector system comprising: a) a first coupling element comprising a housing having a fluid inlet portion and a fluid outlet portion, wherein the fluid outlet portion has a structure comprising one or more openings to allow for the exiting of fluid from the housing, wherein the first coupling element further comprises a spring-loaded valve to prevent fluid from exiting the housing; and b) a second coupling element comprising a second housing having a fluid inlet end and a fluid outlet end, the fluid outlet end configured to displace the spring-loaded valve when inserted into the housing of the first coupling element to generate a coupled state; and wherein the housing of the first coupling element is connected to the fluid collection container, wherein the one or more openings of the fluid outlet portion of the first coupling element is enclosed within the fluid collection container, and uncoupling of the first coupling element and the second coupling element results in minimal fluid contamination on the outer surfaces of the medical appliance. In some embodiments, the second coupling element is a spring-loaded coupling connector.

In some embodiments, each of the first coupling element and the second coupling element are configured to engage with each other in a coupled state. In further embodiments, the first coupling element and the second coupling element are engaged in a coupled state by use of a twist lock-in mechanism; a single cantilever snap-fit mechanism; or a cantilever snap-fit mechanism comprising a plurality of cantilever snaps at the fluid inlet portion of the first coupling element which forms a snap-fit with a sliding cover on the second coupling element.

BRIEF DESCRIPTION OF THE DRAWINGS

FIG. 1 illustrates an exploded view of an embodiment of a spring-loaded bag connector.

FIG. 4C provides a top view of the second coupling element of FIG. 4A.

FIG. 4D provides a cross-sectional side view of the second coupling element of FIG. 4A.

FIG. 5 provides device measurements of an embodiment of a spring-loaded bag connector.

DETAILED DESCRIPTION OF THE INVENTION

Figure 2A:
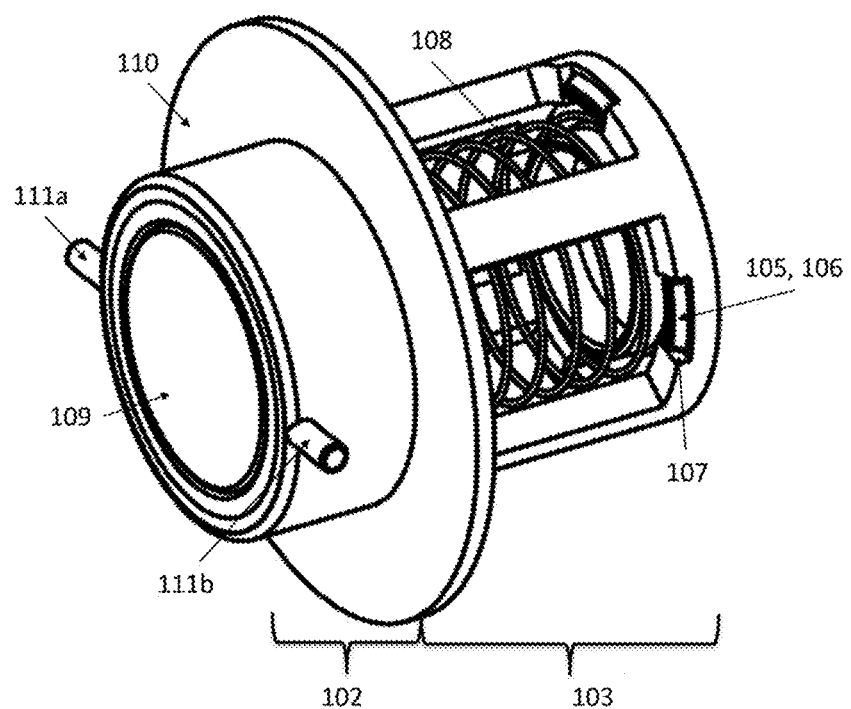
FIG. 2A illustrates a perspective view of the bag connector of FIG. 1 in a closed configuration.

Provided herein, in various embodiments, are bag connector systems useful in a medical appliance. These bag connector systems provide a simple method to connect tubing that directs the flow of waste to an external waste collection container while minimizing the exposure of the waste inside the tubing to the outside environment. In some implementations, the bag connector system comprises a first coupling element and a second coupling element, wherein the first coupling element is a spring-loaded bag connector. The spring-loaded bag connector is configured to be attached, directly or indirectly, to a collection container, wherein the attachment may be permanent or reversible. In some embodiments, a collection container is welded or glued to a spring-loaded bag connector to generate a self-closing collection bag. In some embodiments, the second coupling element is a medical device or component of a medical device useful for facilitating the flow and subsequent collection of waste comprising fluid and/or matter. Examples of second coupling elements or components that are configured to engage with second coupling elements include, without limitation, catheters, catheter adaptors and/or connectors, and medical grade tubing. In an exemplary embodiment, when the two coupling elements of the bag connector system are coupled together, a drainage path between the source of waste (e.g., subject via tubing) and a waste collection container is activated to open. In an additional embodiment, when the two coupling elements of the bag connector system are uncoupled or disconnected, the first coupling element attached to or comprising a waste collection container will return to a closed state, retaining the collected waste in the collection container. In an additional embodiment, the second coupling element is a spring-loaded coupling connector. The second coupling element may be configured to connect to a catheter. When the two coupling elements of the bag connector system are uncoupled or disconnected, both the first coupling element and the second coupling element will each return to a closed state, retaining the collected waste in the collection container with the use of the first coupling element, as well as retaining waste in the catheter with the use of the second coupling element. As such, the exterior surfaces of the bag connector system will have minimum exposure to waste.

Spring-Loaded Bag Connector

Disclosed herein, in certain embodiments, are spring-loaded bag connectors for use in a bag connector system. In some embodiments, the spring-loaded bag connector (or "bag connector") comprises a) a housing having a fluid inlet portion and a fluid outlet portion, wherein the fluid outlet portion has a structure comprising one or more openings to allow for the exiting of fluid from the housing; and b) a spring-loaded valve to regulate the exiting of fluid from the housing; wherein depression of the spring-loaded valve results in an open configuration to allow fluid to exit through the openings of the housing; and wherein decompression of the spring-loaded valve results in a closed configuration to restrict fluid from exiting the housing.

Disclosed herein, in certain embodiments, are self-closing collection bags having a spring-loaded connector design. In some embodiments, the self-closing collection bag comprises a fluid collection bag attached to a bag connector, wherein the bag connector comprises a) a housing having a fluid inlet portion and a fluid outlet portion, wherein the fluid outlet portion has a structure comprising one or more openings to allow for the exiting of fluid from the housing; and wherein the one or more openings of the fluid outlet portion are enclosed within the fluid collection bag; and b) a spring-loaded valve to regulate the exiting of fluid from the housing; wherein depression of the spring-loaded valve results in an open configuration to allow fluid to exit from the housing into the fluid collection bag; and wherein decompression of the spring-loaded valve results in a closed configuration to restrict fluid from exiting the housing. In some instances, the collection bag comprises a deodorizing element, such as a filter or activated charcoal. In some instances, the collection bag is printed with a volume graduation to aid the output measurement. Further provided herein, in some embodiments, are self-closing collection bags comprising a fluid collection bag having a three-dimensional shape and a bag connector, wherein a portion of the bag connector is enclosed within the fluid collection bag. A fluid collection bag with a three-dimensional shape allows for a higher capacity than a two-dimensional bag without an increase in footprint. In some embodiments, a three-dimensional bag comprises a pouch raised by given height in the direction perpendicular to a two-dimensional footprint. Thermoforming or blow-molding are exemplary methods to generate three-dimensional collection bags. Alternatively, pleats or folds may be introduced, in combination with or in addition to thermoforming and blow-molding techniques. The fluid collection bag may also be semi-rigid or rigid in structure. Volume capacity for collection bags having three-dimensional shape may be greater than 0.5 L, 1.0 L, 1.5 L, 2.0 L, 2.5 L, and 3 L, such as about 1.5 L or 1.6 L.

In some embodiments, the spring-loaded valve comprises a spring element and a moving door. In another embodiment, the spring-loaded valve further comprises a spring seat or base. In some embodiments, a portion of or all components of the spring-loaded valve are located within the interior of the bag connector housing. The moving door may be made of a material comprising plastic, silicone, rubber, elastomer or any combination thereof. The spring element may be made of a material comprising a metal or plastic. A metal spring includes, without limitation, magnetic resonance imaging compatible metals, including brass and bronze. An exemplary spring element is a compression spring such as a helical compression spring. Examples of spring elements include, without limitation, straight metal coil, concave (hourglass), conical and convex (barrel) springs. In some embodiments, the spring rate of the spring element is from about 0.009 N/mm (0.05 lbs/in) to about 2.63 N/mm (15 lbs/in), or preferably, from about 0.018 N/mm (0.1 lbs/in) to about 1.4 N/mm (8 lbs/in). In a preferred embodiment, in cases wherein a compression spring is used in both the first coupling element and the second coupling element (e.g., the second coupling element is a spring-loaded coupling connector), the spring rate of the first coupling element is different from the spring rate of the second coupling element. In some embodiments, the spring wire diameter is from about 0.254 mm (0.01 in) to about 1.27 mm (0.05 in). In one example, the maximum load of the compression spring is no more than 8 N, or preferably, no more than 5 N. The compression spring can be selected from metals, such as steel, stainless steel, zinc coated steel spring, bronze, beryllium copper, and the like. An example of a compression spring useful in the first coupling element is B18-197, a zinc coated steel spring made by Century Spring Corp. in Los Angeles, Calif.

The bag connector, in various embodiments, comprises a base. In an exemplary embodiment, the base is connected to the bottom end of the housing at the fluid outlet portion. In some embodiments, the housing comprises or is permanently connected to the base. In another embodiment, the base is removably connected to the housing. In some embodiments, the base comprises a plurality of cantilever snaps to form a snap-fit with a ridge at the bottom of the fluid outlet portion of the housing. In a further embodiment, the base is a component of the spring-loaded valve, wherein the base provides a support for the spring element. In some embodiments, the base is ultrasonically welded to the bottom end of the fluid outlet portion of the housing. In some embodiments, the base is glued to the bottom end of the fluid outlet portion of the housing. In some cases, the diameter of the base is from about 20 mm to about 60 mm, from about 20 mm to about 50 mm, from about 20 mm to about 40 mm, or from about 25 mm to about 40 mm. For example, the base may be about 25 mm, 26 mm, 27 mm, 28 mm, 29 mm, 30 mm, 31 mm, 32 mm, 33 mm, 34 mm, 35 mm, 36 mm, 37 mm, 38 mm, 39 mm or 40 mm in diameter. In some embodiments, the aforementioned diameter of a base is exclusive of any base connecting elements such as snaps. In some cases, the base comprises one or more snaps, wherein each snap has a height from about 1 mm to about 10 mm or from about 1 mm to about 5 mm. For example, each snap has a height of about 2 mm, 3 mm, 4 mm or 5 mm. In some cases, the fluid outlet portion of the housing comprises a ridge, wherein the ridge comprises one or more seats. One or more snaps of a base may sit in the one or more seats of the ridge to connect the base to the fluid outlet portion. In some instances, the height of a ridge is greater than the height of a snap. For example, the height of a ridge is from about 2 mm to about 12 mm, from about 2 mm to about 10 mm, or from about 2 mm to about 8 mm. In some cases, the height of a ridge is about 2 mm, 3 mmm, 4 mm, 5 mm, 6 mm, 7 mm or 8 mm. In some embodiments, the diameter of the bottom of the fluid outlet portion, wherein the bottom of the fluid outlet portion optionally comprises a base (e.g., a removable base), is from about 20 mm to about 60 mm, from about 20 mm to about 50 mm, from about 20 mm to about 40 mm, or from about 25 mm to about 40 mm. For example, the bottom of the fluid outlet portion may be about 30 mm, 31 mm, 32 mm, 33 mm, 34 mm, 35 mm, 36 mm, 37 mm, 38 mm, 39 mm or 40 mm in diameter.

The housing of the bag connector may be constructed of any material suitable for containing fluid and/or matter. For example, the housing of the bag connector is comprised of a plastic. Non-limiting examples of plastics useful as the housing of the bag connector include polyethylene, polypropylene, ABS, nylon, PET, PVC and other like plastic materials. In some embodiments, the fluid inlet portion of the housing has a wall of solid construction, so that fluid and/or matter within the interior of the fluid inlet portion is not exposed to the external environment. In some embodiments, the fluid outlet portion of the housing has a plurality of openings in its structure. In some embodiments, the fluid outlet portion of the housing comprises at least 1, at least 2, at least 3, at least 4, at least 5, at least 10, at least 15 or at least 20 openings. In some embodiments, the fluid outlet portion of the housing comprises 1, 2, 3, 4, 5, 6, 7, 8, 9 or 10 openings. The openings may be of any size suitable to allow for the exiting of fluid and/or matter from the fluid outlet portion of the housing. It is to be understood that the size of the openings may be smaller or larger depending on the components of the fluid and/or matter to be collected, and/or depending on the flow rate of fluid to be collected. For example, the fluid outlet portion openings are smaller in a bag connector suitable for use with a urinary catheter than the openings in a bag connector suitable for use with a rectal catheter. In some cases, the width of an opening is from about 10 mm to about 40 mm, from about 10 mm to about 30 mm, from about 10 mm to about 25 mm, from about 15 mm to about 30 mm, from about 20 mm to about 30 mm, or from about 20 mm to about 25 mm. For example, the width of an opening is about 15 mm, 16 mm, 17 mm, 18 mm, 19 mm, 20 mm, 21 mm, 22 mm, 23 mm, 24 mm or 25 mm.

In an exemplary embodiment, the inner diameter at the opening of the fluid inlet portion of a bag connector is from about 10 mm to about 40 mm, from about 15 mm to about 35 mm, preferably from about 20 mm to about 35 mm. For example, the diameter of the opening of the fluid inlet portion is about 25 mm, 26 mm, 27 mm, 28 mm, 29 mm, 30 mm, 31 mm, 32 mm, 33 mm, 34 mm, 35 mm, or any value between, such as 27.7 mm. In another exemplary embodiment, the inner diameter of the fluid outlet portion (e.g., a barrel element) of a bag connector is from about 10 mm to about 40 mm, from about 15 mm to about 35 mm, preferably from about 25 mm to about 35 mm. For example, the inner diameter of the fluid outlet portion is about 25 mm, 26 mm, 27 mm, 28 mm, 29 mm, 30 mm, 31 mm, 32 mm, 33 mm, 34 mm, 35 mm, or any value between, such as 29.8 mm. The inner diameter of the fluid outlet portion may be such that the moving door can move along the inside of the fluid outlet portion of the housing to close the slightly smaller diameter of the fluid inlet portion of the housing. Likewise, the diameter of the fluid outlet portion may be such that the moving door can move toward the base of the housing to allow the bag connector to be in an open configuration. In another embodiment, the fluid inlet portion is designed with a circumference of a recess such that it can help seal against the fluid when a first coupling element and a second coupling element are connected. In some cases, the recess is a depression at the top of the fluid inlet portion, wherein the depression is less than about 5 mm, 4 mm, 3 mm, 2 mm, or 1 mm in depth. For example, the recess is about 0.5 mm, 0.6 mm, 0.7 mm, 0.8 mm, 0.9 mm or 1 mm in depth.

The liquid tight or sealing feature of the methods and devices disclosed herein may be further enhanced by varying the hardness of the material (e.g., plastics) between the housing and moving door. For example, the hardness of the harder material can be in the range of Shore D 30 (equivalent to Shore A 80) to Shore D 80, or about Shore D 30, about Shore D 40, about Shore D 50, about Short D 60, about Shore D 70 or about Shore D 80, while the hardness of the softer material can be in the range of Shore A 30 to Shore A 90, or about Shore A 30, about Shore A 40, about Shore A 50, about Shore A 60, about Shore A 70 or less than Shore A 80. In other embodiments, the liquid tight feature may be further enhanced by using a two-shot molded housing or moving door, wherein a softer component in the housing or moving door, or both, can be incorporated with a two-shot injection mold to create a liquid tight closure system. In still other embodiments, the liquid tight feature can be further enhanced by adding an O-ring or other elasticized seal between the housing and the moving door. In still other embodiments, the liquid tight feature of the devices and methods disclosed herein may be further enhanced by transforming the contents inside the collection bag, e.g., use of a superabsorbent sachet (for example, ConvaTec Diamonds) inside the collection bag, which gels the contents of the bag. In this instance, the superabsorbent component can be added when the bag is first assembled, or at the time of use by a user, e.g., a clinician or nurse practitioner.

In certain embodiments, the length of a bag connector from the top of the fluid inlet portion to the bottom of the fluid outlet portion (or base connected to the bottom of the fluid outlet portion), herein "bag connector length", is from about 20 mm to about 100 mm, from about 20 mm to about 90 mm, from about 20 mm to about 80 mm, from about 30 mm to about 80 mm, from about 40 mm to about 80 mm, from about 20 mm to about 70 mm, from about 20 mm to about 60 mm, from about 30 mm to about 60 mm, or from about 40 mm to about 50 mm. For example, the bag connector length is about 45 mm, 46 mm, 47 mm, 48 mm, 49 mm or 50 mm. In some cases, the bag connector length is less than about 100 mm, 90 mm, 80 mm, 70 mm, 60 mm, 50 mm or 40 mm. In certain embodiments, the length of the fluid inlet portion of a bag connector is from about 5 mm to about 50 mm, from about 5 mm to about 40 mm, from about 5 mm to about 30 mm, or from about 5 mm to about 20 mm. For example, the length of the fluid inlet portion is about 10 mm, 11 mm, 12 mm, 13 mm, 14 mm, 15 mm, 16 mm, 17 mm, 18 mm, 19 mm, 20 mm or any value between, such as 14.5 mm. In some instances, the length of the fluid inlet portion spans from the top of the bag connector housing to the top of an attachment fixture for attaching a fluid collection bag to the bag connector. In certain embodiments, the outer diameter of the top of a bag connector is from about from about 20 mm to about 60 mm, from about 20 mm to about 50 mm, from about 20 mm to about 40 mm, or from about 25 mm to about 40 mm. For example, the outer diameter of the top of the bag connector may be about 25 mm, 26 mm, 27 mm, 28 mm, 29 mm, 30 mm, 31 mm, 32 mm, 33 mm, 34 mm, 35 mm, 36 mm, 37 mm, 38 mm, 39 mm or 40 mm in diameter. In some cases, the outer diameter of the top of a bag connector is similar to the diameter of the base of the bag connector, for example, there is less than a 50%, 40%, 30%, 20%, or 10% difference between the diameters.

The bag connector, in various embodiments, comprises a fixture for attachment to a fluid collection bag. An exemplary fixture is a flange that may be connected to a collection bag using, for example, an adhesive (i.e., gluing), heat welding, or ultrasonic welding. In some embodiments, the housing of the bag connector comprises a flange, wherein the flange is attached, directly or indirectly, to a fluid collection bag. In some instances, the collection bag comprises a deodorizing element, such as a filter or activated charcoal. In some embodiments, the fluid collection bag is welded to the flange. In another embodiment, the fluid collection bag is removably attached to the flange. The width of the flange may span from about 2 mm to about 30 mm, from about 2 mm to about 25 mm, from about 2 mm to about 20 mm, from about 2 mm to about 15 mm, from about 2 mm to about 10 mm, from about 5 mm to about 30 mm, from about 5 mm to about 25 mm, from about 5 mm to about 20 mm, from about 5 mm to about 15 mm, from about 5 mm to about 10 mm, from about 7 mm to about 20 mm, from about 7 mm to about 15 mm, from about 8 mm to about 15 mm, and from about 8 mm to about 12 mm. In some instances, the width of the flange is about 5 mm, about 6 mm, about 7 mm, about 8 mm, about 9 mm, about 10 mm, about 11 mm, about 12 mm, about 13 mm, about 14 mm, or about 15 mm. In some cases, the length or height of the flange is less than about 10 mm, 9 mm, 8 mm, 7 mm, 6 mm, 5 mm, 4 mm, or 3 mm. In some cases, the length of the flange is from about 1 mm to about 10 mm or from about 1 mm to about 5 mm; for example, 1 mm, 2 mm, 3 mm, 4 mm or 5 mm. In some instances, the outer diameter of an attachment fixture such as a flange is less than about 100 mm, 90 mm, 80 mm, 70 mm, 60 mm, 50 mm or 40 mm. In some embodiments, the outer diameter of a flange is from about 20 mm to about 100 mm, from about 30 mm to about 100 mm, from about 40 mm to about 100 mm, from about 40 mm to about 90 mm, from about 40 mm to about 80 mm, from about 50 mm to about 70 mm, or any value between such as about 55 mm, 56 mm, 57 mm, 58 mm, 59 mm, 60 mm, 61 mm, 62 mm, 63 mm, 64 mm or 65 mm.

The bag connector, in various embodiments, is connected to or comprises a fluid collection container or collection bag. The collection container includes any container suitable for the collection and/or storage of medical waste, for example fluids and fluids comprising particulate or solid matter. Examples of collection containers include, without limitation, urinary collection bags and fecal matter collection bags. In exemplary embodiments, the collection containers are configured to collect waste externally from a subject. The collection containers may be made of a material comprising plastic, such polyethylene, polypropylene, EVA, ABS, nylon, PET, PVdC (polyvinylidene chloride), PVT, or mixtures or multilayer films thereof. In some embodiments, the bag is constructed to form a three-dimensional shape since a portion of the bag connector is recessed into the inside of the bag. Such a three-dimensional shape of the collection bag can increase the bag capacity without any change in the footprint (i.e., length and width) of the collection bag. In some embodiments, the collection bag is thermoformed. In other embodiments, the collection bag is blow-molded. In yet other embodiments, the collection bags may comprise folds or pleats to enable volume expansion. In still other embodiments, the collection bag is rigid or semi-rigid in structure. In additional embodiments, the collection bag may require additional structures, including supporting straps or fixtures, to properly support the connected collection bag when filled. In still other embodiments, the collection bag may comprise further supporting structures to allow placement of the collection bag in or on a secured space (e.g., a floor, a shelf or other supporting structure).

In some instances, the collection bag comprises a deodorizing element, such as a filter or activated charcoal. As used herein, at least in certain embodiments, a fluid comprises liquid, or liquid and matter. For example, a fluid is any medical waste removed from a subject such as a human.

The bag connector, in various embodiments, comprises an engaging element useful for coupling the bag connector to a second coupling element. In some embodiments, the engaging element comprises one or more prongs for engaging with a second coupling element in a twist lock-in mechanism. The prongs for use in a twist-lock mechanism may reside either in the first coupling element or in the second coupling element. In another embodiment, the bag connector is maintained in a coupled state with a second coupling element by use of a snap-fit mechanism, wherein one of the coupling elements comprises at least one cantilever snap and the other coupling element comprises a ridge suitable for engaging with the one or more cantilever snaps. In some cases, the diameter of a prong is less than about 10 mm, 9 mm, 8 mm, 7 mm, 6 mm, 5 mm, 4 mm, or 3 mm. In some cases, the diameter of a prong is from about 1 mm to about 10 mm or from about 1 mm to about 5 mm; for example, 1 mm, 2 mm, 3 mm, 4 mm or 5 mm. In an embodiment wherein the bag connector comprises at least two prongs, the distance between the outer edges of two prongs 180° apart is from about 30 mm to about 100 mm, from about 30 mm to about 90 mm, from about 30 mm to about 80 mm, from about 30 mm to about 70 mm, from about 30 mm to about 60 mm or from about 30 mm to about 50 mm. In some cases, the distance is less than about 80 mm, 70 mm, 60 mm, 50 mm, 40 mm, or 30 mm.

An embodiment of a spring-loaded bag connector is illustrated in FIG. 1. The bag connector 100 comprises a housing 101 suitable for the passage of fluid and/or matter from the fluid inlet portion 102 to the fluid outlet portion 103. In some cases, the fluid outlet portion is referred to as a barrel element 103. Housing 101 may be made of plastic or any material suitable for containing and directing fluid. The fluid outlet portion 103 has openings 104 in its structure to allow for the passage of fluid and/or matter from the interior of the housing to the exterior of the housing through the openings. In FIG. 1, the bag connector comprises a base 105 configured for connection to the bottom of the housing 101, in particular, to the end of the fluid outlet portion 103. In this figure, the base 105 comprises a plurality of cantilever snaps 106 which form a snap-fit with seats 107 at the bottom of the fluid outlet portion of the housing 101.

In the bag connector embodiment illustrated in FIG. 1, the bag connector comprises a spring 108 configured for placement within the interior of the housing 101. In this embodiment, the bag connector further comprises a moving door 109 configured for placement within the interior of the housing 101.

In some embodiments, the base (e.g., 105) provides support to the spring (e.g., 108), wherein the spring is connected to, or rests upon, the base. In some embodiments, the spring (e.g., 108) provides support to the moving door (e.g., 109), wherein the spring is connected to or rests upon the moving door.

In some embodiments, the bag connector comprises a spring-loaded valve comprising a spring (e.g., 108) and a moving door (e.g., 109). In some embodiments, the moving door and the spring are an integrated piece or separately manufactured pieces joined together. In some embodiments, the moving door (e.g., 109) automatically provides a seal within the housing (e.g., 101) which prevents the exit of fluid from the housing through the fluid outlet portion (e.g., 103).

In various embodiment, the housing of a bag connector comprises an attachment fixture to connect a fluid collection bag to the housing, for example on the exterior of the housing. In FIG. 1, the bag attachment fixture is a flange 110. In some embodiments, the bag attachment fixture is positioned between the fluid inlet and fluid outlet portions on a central portion of the bag connector housing. In other embodiments, the bag attachment fixture is a component of or is located on/within the fluid inlet portion of the bag connector housing. In other embodiments, the bag attachment fixture is a component of or is located on/within the fluid outlet portion of the bag connector housing. The bag attachment fixture, e.g., flange, in some instances, is welded to a fluid collection bag (not shown). In other instances, the bag attachment fixture is removably connected to a fluid collection bag (not shown). In an exemplary embodiment, when the fluid collection bag is affixed to the housing, by flange or by other means, the fluid outlet portion may be wholly or partially enclosed within the inside of the bag. Therefore, when the bag connector is in an open configuration, fluid and/or matter is able to pass from the interior of the housing, through the openings of the fluid outlet portion, and into the fluid collection bag.

In some embodiments, the housing of the bag connector comprises an engaging element. In some embodiments, the bag connector is a first coupling element and the engaging element of the bag connector is configured to engage with a second coupling element. As shown in FIG. 1, an engaging element may comprise one or more prongs 111. In an exemplary embodiment, when the engaging element of the bag connector is coupled with a second coupling element, the moving door (e.g., 109) is depressed toward the base (e.g., 105) of the bag connector housing (e.g., 101) and the bag connector is in an open position. In some embodiments, the second coupling element comprises a protrusion (in some instances, a fluid outlet end) having a diameter suitable for insertion into the interior of the bag connector housing. In this instance, the protrusion is inserted into the housing during engagement (or coupling), resulting in the depression of the moving door and compression of the spring. In some embodiments, the protrusion of the second coupling element comprises openings which in part or wholly match with the openings of the fluid outlet portion of the bag connector. When the moving door is depressed, either partially or completely compressing the spring, the bag connector is in an open configuration. In an open configuration, fluid and/or matter is able to pass from within the interior of the housing to the exterior of the housing. In some embodiments, there are varying degrees of open configurations, wherein each open configuration may allow for a different rate of fluid exiting from the bag connector housing. In additional embodiments, there are varying degrees of open configurations, wherein each open configuration may allow for a different size of fluid and/or matter to exit the bag connector housing. In an exemplary embodiment, when the bag connector is engaged with a second coupling element, for example a spring-loaded coupling connector configured to further attach to a catheter, fluid and/or matter is able to pass from the second coupling element through the interior of the bag connector housing to the exterior of the bag connector housing. In many instances, the housing is connected to a collection bag, for example, by a flange, allowing for the passage of fluid and/or matter from the second element into the collection bag. When the second coupling element is disengaged from the bag connector, the protrusion no longer compresses the moving door and the moving door is released into a closed configuration. In many configurations, the moving door (e.g., 109) is located within the fluid inlet portion of the bag connector housing (e.g., 101) in the closed configuration, wherein the entire outer edge of the moving door (e.g., 112) creates a seal with the interior wall of the fluid inlet portion of the bag connector housing. In this instance, the closed configuration may provide an air-tight seal. In other instances, the closed configuration provides a fluid seal. For example, a seal can be maintained by the use of an O-ring.

Figure 2B:
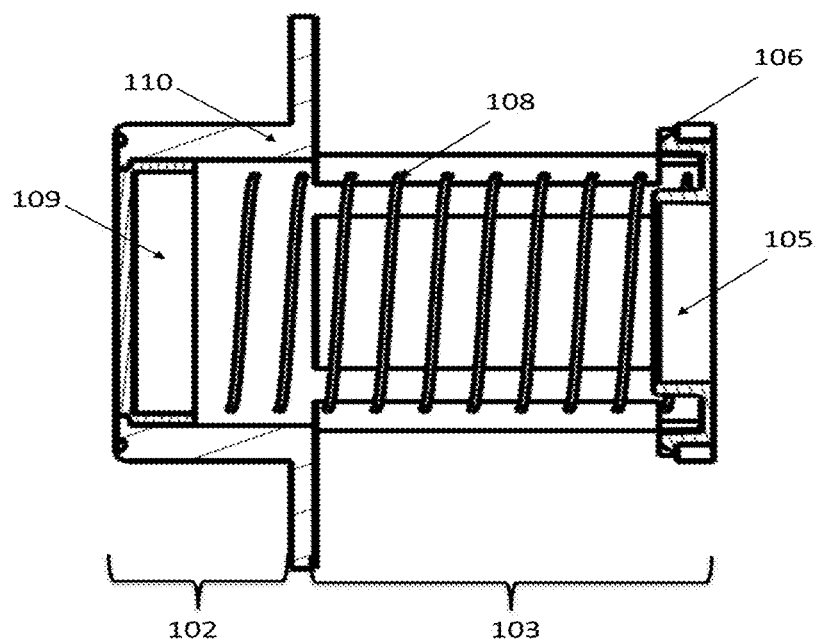
FIG. 2B illustrates a cross-sectional view of the bag connector of FIG. 1 in a closed configuration.

A perspective view of an assembled bag connector of FIG. 1 in a closed configuration is illustrated in FIG. 2a. FIG. 2b illustrates a cross-sectional view of the bag connector of FIG. 1 in a closed configuration. In these exemplary embodiments, the spring 108 and moving door 109 are located within the interior of the housing 101. In these embodiments, the base 105 is connected to the bottom end of the housing at the fluid outlet portion. The base, in these figures, comprises a plurality of cantilever snaps 106 which connect with the plurality of seats 107 of the fluid outlet portion of the housing 101. In the closed configuration illustrated in FIGS. 2a and 2b, the moving door 109 and spring 108 are not compressed and the moving door is located at the fluid inlet portion 102 of the housing 101. In this closed configuration, no or minimal fluid and/or matter is able to pass between the exterior surfaces of the fluid inlet portion of the housing and the interior surfaces of the fluid inlet portion of the housing.

Figure 3A:
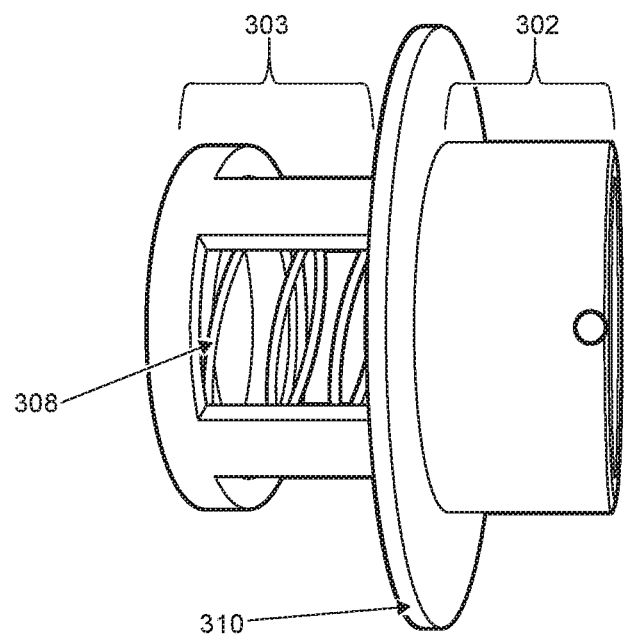
FIG. 3A provides a side view of an embodiment of a spring-loaded bag connector in a closed configuration.
Figure 3B:
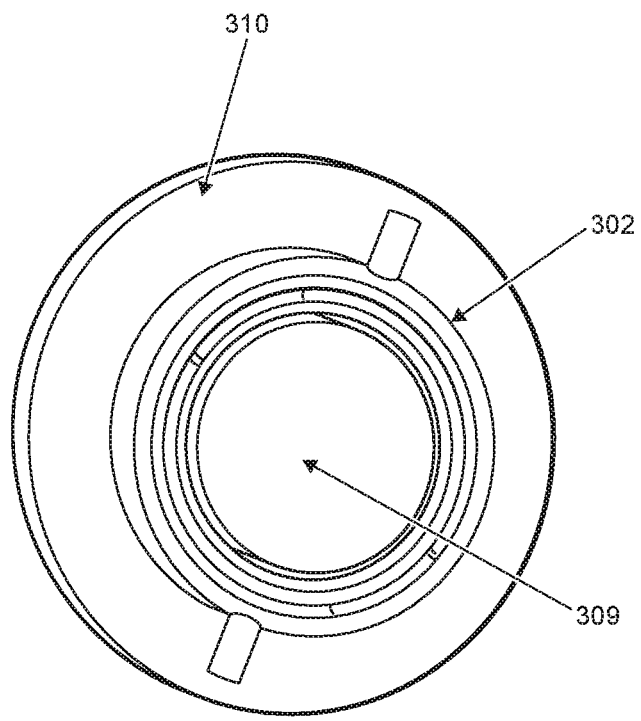
FIG. 3B provides a top view of an embodiment of the spring-loaded bag connector in a closed configuration.
Figure 3C:
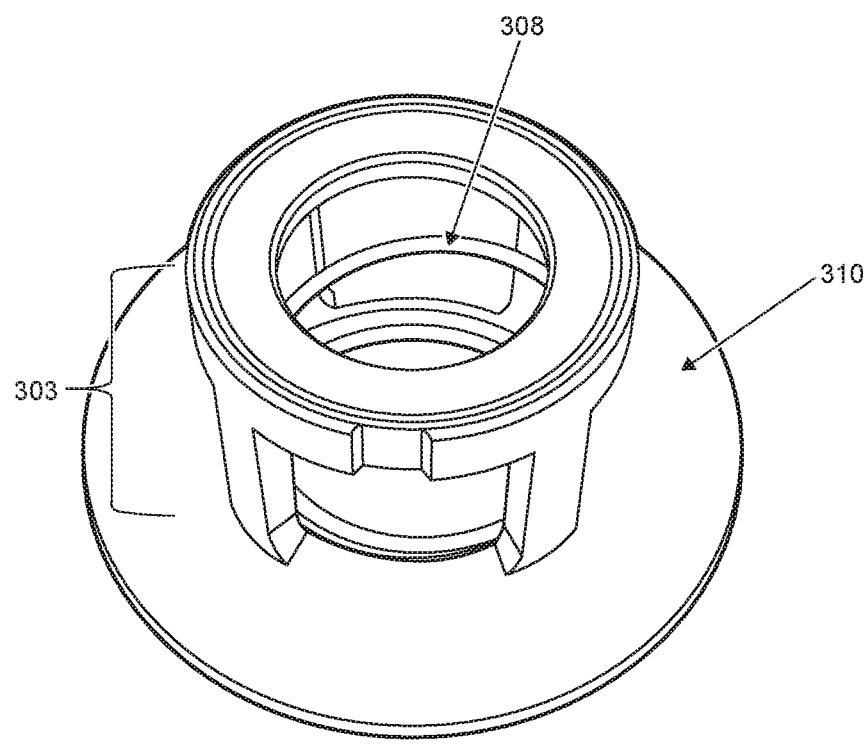
FIG. 3C provides a bottom view of an embodiment of a spring-loaded bag connector in a closed configuration.
Figure 3D:
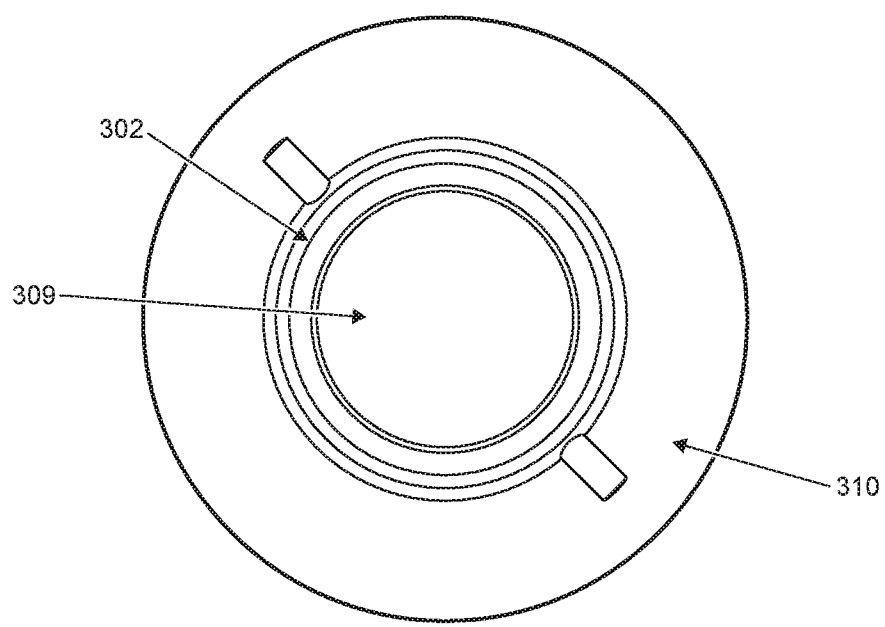
FIG. 3D provides a top view of an embodiment of a spring-loaded bag collector manually pressed into an open configuration by a finger.

A side view of an embodiment of a bag connector in a closed configuration is shown in FIG. 3a. In this figure, the bag connector is in a closed state and the spring 308 is relaxed. FIG. 3b illustrates a top view of the embodiment of the bag connector shown in FIG. 3a, wherein the bag connector is in a closed state and the moving door 309 is located at the fluid inlet portion 302 of the bag connector housing, and wherein the moving door 309 is aligned within the interior of the bag connector housing to generate a seal. In some embodiments, the seal does not allow the passage of air between the exterior of the housing and the interior of the housing. In other or additional embodiments, the seal does not allow for the passage of fluid and/or matter between the exterior of the housing and the interior of the housing. In other or additional embodiments, the seal allows for the passage of minimal amounts of fluid and/or matter between the exterior of the housing and the interior of the housing. FIG. 3c illustrates a bottom view of the embodiment of the bag connector shown in FIG. 3a in a closed configuration. FIG. 3d illustrates a top view of the embodiment of a bag collector of FIG. 3a, wherein the bag collector is manually pressed into an open state by a finger. In FIG. 3d, a force is applied to the moving door 309 to depress the moving door and spring 308 from the top of the fluid inlet portion 302 toward the bottom of the fluid outlet portion within housing 301.

The bag connector of FIGS. 3a to 3d comprises a housing 301 having a fluid inlet portion 302 and a fluid outlet portion 303. The housing 301 further comprises a flange 310 useful for attaching the bag connector to a fluid collection bag. In this embodiment, the wall of the fluid inlet portion 302 is solid, prohibiting the passage of fluid and/or matter between the interior of the fluid inlet portion to the exterior of the fluid inlet portion. In this embodiment, the wall of the fluid outlet portion comprises one or more openings 304, allowing for the passage of fluid and or matter between the interior of the fluid outlet portion and the exterior of the fluid outlet portion. In FIGS. 3b and 3d, an engaging element is shown, wherein the engaging element comprises two prongs 311 for coupling the bag connector to a second coupling element. For example, the engaging element is configured to engage with a second coupling element, as embodied in FIG. 4a. In FIG. 3c, a seat 307 is shown, wherein the seat is located at the bottom of the housing 301 and is configured to connect with a cantilever snap. In some embodiments, the cantilever snap is a component of a base, suitable to enclose the bottom of the housing upon connection with the housing.

Dimensions of an embodiment of a bag connector are shown in FIG. 5. Bag connector 500 comprises a housing 501 comprising a fluid inlet portion 502 and a fluid outlet portion 503. At the opening end of the fluid inlet portion, there is a recess 515. The housing 501 further comprises a flange 510. The bag connector 500 comprises a base 505 connected at the bottom end 514 of the fluid outlet portion by a plurality of snaps 506 on the base 505. Each snap is configured to rest on a seat of a fluid outlet portion ridge 513, creating a snap-fit connection between the base 505 and the housing 501. The fluid outlet portion comprises a plurality of openings 504. The bag connector housing 501 further comprises prongs 511.

Bag Connector System

Disclosed herein, in certain embodiments, are medical device systems for the management of fecal or urinary waste. In some embodiments, a medical device system disclosed herein is a bag connector system. In one aspect, a bag connector system comprises a) a first coupling element comprising a housing having a fluid inlet portion and a fluid outlet portion, wherein the fluid outlet portion has a structure comprising one or more openings to allow for the exiting of fluid from the housing, wherein the first coupling element further comprises a spring-loaded valve to prevent fluid flow from exiting the housing, and wherein one or more components of the spring-loaded valve are located within the housing; and b) a second coupling element comprising a second housing having a fluid inlet end and a fluid outlet end, the fluid outlet end configured to displace the spring-loaded valve when inserted into the housing of the first coupling element to generate a coupled state. In an exemplary embodiment, when the coupling elements are in a coupled state, the bag connector system is in an opened configuration and fluid and/or matter is able to exit from the housing of the first coupling element. In a further embodiment, when the coupling elements are not in a coupled state or not connected, the bag connector system is in a closed configuration and fluid and/or matter is not able to exit from the housing of the first coupling element. In various embodiments, the first coupling element is connected to or comprises a collection container. In this embodiment, the fluid outlet portion of the first coupling element is enclosed within the collection container. Therefore, in this instance, when the coupling elements are in an open configuration, fluid and/or matter is able to exit from within the housing of the first coupling element to the interior of the fluid collection contain. In addition, wherein the coupling elements are in a closed configuration, fluid and/or matter is not able to exit from within the housing of the first coupling element, resulting in minimal fluid and/or matter contamination to the outside environment (for example, outside of the collection bag). In some embodiments, the second coupling element is a spring-loaded coupling connector comprising a second spring-loaded valve, wherein when the coupling elements are in a coupled state, the spring-loaded coupling connector is in an open configuration and fluid is able to exit from the housing of the second coupling element to the housing of the first coupling element. In additional embodiments, when the coupling elements are not in a coupled state, the second coupling element, e.g., spring-loaded coupling connector, is in a closed configuration and fluid is not able to exit from the second housing. In some embodiments, the second spring-loaded valve of the spring-loaded coupling connector is compressed during coupling with the first coupling element, wherein the fluid inlet portion of the first coupling element presses against the second spring-loaded valve of the spring-loaded coupling connector; to generate an open configuration in the spring-loaded coupling connector.

In an exemplary embodiment, the first coupling element is a spring-loaded bag connector as described above. In another embodiment, the first coupling element is a self-closing collection bag as described above. In an exemplary embodiment, the second coupling element comprises a catheter and/or catheter adaptor. For example, a catheter adaptor may include any device configured to attach, either directly or indirectly, to a catheter or component of a catheter. In another embodiment, the second coupling element is a tube or tube adaptor. For example, a tube adaptor may include any device configured to attach to a tube, including, without limitation, a catheter. In another or further embodiment, the second coupling element is connected to or comprises, irreversibly or reversibly, tubing. Tubing includes all medical grade tubing, in particular tubing used for the collection of human waste. In some embodiments, the second coupling element is a spring-loaded coupling connector. In some embodiments, the spring-loaded coupling connector is further configured to connect to a catheter and/or medical grade tubing. In some embodiments, the fluid inlet end of the second coupling element is connected, directly or indirectly, to a first end of a tube and/or catheter, wherein the second end of the tube and/or catheter is connected, directly or indirectly, to a subject for the collection of waste.

The first coupling element, in various embodiments, comprises a fixture for attachment to a fluid collection bag. In some instances, the second coupling element comprises a fixture for attachment to a fluid collection bag. An exemplary attachment fixture includes a flange. In some embodiments, the housing of the first coupling element comprises a flange, wherein the flange is attached, directly or indirectly, to a fluid collection bag. In some embodiments, the fluid collection bag is welded to the flange. In another embodiment, the fluid collection bag is removably attached to the flange. The width of the flange may span from about 2 mm to about 30 mm, from about 2 mm to about 25 mm, from about 2 mm to about 20 mm, from about 2 mm to about 15 mm, from about 2 mm to about 10 mm, from about 5 mm to about 30 mm, from about 5 mm to about 25 mm, from about 5 mm to about 20 mm, from about 5 mm to about 15 mm, from about 5 mm to about 10 mm, from about 7 mm to about 20 mm, from about 7 mm to about 15 mm, from about 8 mm to about 15 mm, and from about 8 mm to about 12 mm. In some instances, the width of the flange is about 5 mm, about 6 mm, about 7 mm, about 8 mm, about 9 mm, about 10 mm, about 11 mm, about 12 mm, about 13 mm, about 14 mm, or about 15 mm.

The first coupling element, in various embodiments, is connected to or comprises a fluid collection container or collection bag. In other embodiments, the second coupling element is connected to or comprises a fluid collection container. The collection container includes any container suitable for the collection and/or storage of medical waste, for example fluids and fluids comprising particulate matter. Examples of collection containers include, without limitation, urinary collection bags and fecal matter collection bags. In exemplary embodiments, the collection containers are configured to collect waste externally from a subject. The collection containers may be made of a material comprising plastic. Non-limiting examples of suitable plastic material include polyethylene, polypropylene, EVA, ABS, nylon, PET, PVdC (polyvinylidene chloride), PVC, and the like.

In some embodiments, the spring-loaded valve functions as a self-closing seal. In exemplary embodiments, the uncoupling of the first coupling element and the second coupling element results in minimal fluid contamination on the outermost surfaces of the coupling elements. In some embodiments, a portion of or all of the outer surfaces of the fluid outlet portion of the first coupling element is enclosed within a fluid collection container. In some embodiments, the exterior of the system, or outside environment, comprises the fluid inlet portion of the first coupling element. In some embodiments, the exterior of the system comprises the fluid inlet end of the second coupling element. In some embodiments, the first coupling element is a self-closing collection bag. In some embodiments, the first coupling element comprises or is connected to a collection container. In some embodiments, the exterior of the system (also outer surfaces or outside environment), comprises the exterior surface of a collection container, wherein the collection container may enclose one or more portions of the first coupling element, including, without limitation the fluid outlet portion or region of the fluid outlet portion. In some cases, the collection container encloses one or more portions of the second coupling element, including, for example, the fluid outlet end or region of the fluid outlet end.

In some embodiments, minimal fluid contamination on the outer surfaces of the coupling elements upon uncoupling of the first coupling element and second coupling element is little to no detectable fluid contamination on the outer surfaces of the coupling elements. In some embodiments, minimal fluid contamination on the outer surfaces of the coupling elements upon uncoupling of the first coupling element and second coupling element is negligible or limited fluid contamination on the outer surfaces of the coupling elements. In some embodiments, minimal fluid contamination on the outer surfaces of the coupling elements upon uncoupling of the first coupling element and second coupling element is little to no detectable fluid contamination to negligible or limited fluid contamination on the outer surfaces of the coupling elements.

In some embodiments, the bag connector system does not have a split valve design.

In some embodiments, the housing of the second coupling element is made of plastic or any other suitable material for containing and directing fluid, or a combination of such suitable materials. For example, the housing of the second coupling element is comprised of a plastic. Non-limiting examples of suitable plastic material include polyethylene, polypropylene, EVA, ABS, nylon, PET, PVC and the like. In some embodiments, the fluid inlet end of the second coupling element has a wall of solid construction, so that fluid and/or matter within the interior of the fluid inlet end is not exposed to the external environment. In some embodiments, the fluid outlet end of the second coupling element has one or more openings in its structure. In some embodiments, the fluid outlet end of the second coupling element has openings that correspond to openings in the fluid outlet portion of the first element. In another embodiment, the fluid outlet end of the second coupling element has a wall of solid construction. In an exemplary embodiment, the diameter of the fluid outlet end of a second coupling element prototype is from about 10 mm to about 40 mm, from about 20 mm to about 30 mm, preferably from about 25 mm to about 30 mm, or about 27.4 mm. In one example, the diameter of the fluid outlet end of the second coupling element is slightly smaller (e.g., less than about 10%, 5%, 4%, 3%, 2%, 1% or 0.5% smaller) than the entrance of a bag connector element. As an example, the entrance of the bag connector is about 27.7 mm and the diameter of the fluid outlet end of the second coupling element is about 27.4 mm.

In some embodiments, the spring-loaded valve comprises a moving door and a spring element. In some embodiments, the moving door and spring element are joined to form a unitary object. In other embodiments, the moving door and spring element are separate objects in direct contact with one another. In some embodiments, the moving door is made of plastic, including but not limited to polyethylene, polypropylene, EVA, ABS, nylon, PET, PVdC (polyvinylidene chloride), PVC and the like, or other suitable material such as silicone, rubber or other elastomer. In some embodiments, the spring element is made of metal or plastic. In some embodiments the spring-loaded valve is an integrated piece or may comprise separately manufactured pieces joined together. In some embodiments, the spring-loaded valve comprises a spring seat. In some embodiments, the spring seat is a base configured to attach, permanently or reversibly, to the bottom of the bag connector housing at the fluid outlet portion. In some embodiments, the spring seat is a base, wherein the base is a component of the housing. In further embodiments, the spring-loaded valve is a poppet valve.

In some embodiments, each of the first coupling element and the second coupling element further comprises an engaging element to maintain the first coupling element and the second coupling element in a coupled state. In some embodiments, the first coupling element and the second coupling element are maintained in a coupled state by a locking mechanism. In some embodiments, the locking mechanism is selected from a twist lock-in (bayonet latch) mechanism, a single cantilever snap-fit mechanism, a multiple cantilever snap-fit mechanism, an annular snap-fit mechanism, or an interference fit mechanism. In some embodiments, the locking mechanism is a twist lock-in mechanism. In some embodiments, the locking mechanism is a single cantilever snap-fit mechanism. In some embodiments, the locking mechanism comprises a plurality of cantilever snaps at the fluid inlet portion of the first coupling element which forms a snap-fit with a sliding cover of the second coupling element. In some embodiments, the first coupling element and the second coupling element further comprise complementary components of a locking mechanism. In further embodiments, components of a locking mechanism are part of the fluid inlet portion of the first coupling element and part of the fluid outlet end of the second coupling element. In some embodiments the first coupling element further comprises at least one O-ring. In some embodiments, the second coupling element further comprises at least one O-ring positioned on the outer surface of its housing. In some embodiments, the O-ring is made of silicone, rubber, fluoropolymer, or other elastomer.

In some embodiments, the second coupling element further comprises a sliding cover positioned over the fluid outlet end. In some embodiments, the sliding cover is made of plastic or other suitable material, or combination of such materials. In some embodiments, the sliding cover is self-closing and is connected to a spring element.

In some embodiments, the second coupling element further comprises a check valve. In some embodiments, the check valve is a ball check valve, a diaphragm check valve, a swing check valve, a stop-check valve, a lift-check valve, an in-line check valve or a duckbill valve. In some embodiments, the check valve is a ball check valve. In some embodiments, the check valve is a diaphragm check valve. In some embodiments, the check valve is a swing check valve. In some embodiments, the check valve is a stop-check valve. In some embodiments, the check valve is a lift-check valve. In some embodiments, the check valve is an in-line check valve. In some embodiments, the check valve is a leaf valve. In some embodiments, the check valve is a duckbill valve.

Second Coupling Element

Disclosed herein, in certain embodiments, are second coupling elements configured to connect to bag connectors, e.g., any of the bag connectors described herein, for use in a bag connector system. In some embodiments, the second coupling element comprises a second housing having a fluid inlet end and a fluid outlet end, wherein the fluid outlet end has a structure comprising one or more openings to allow for the exiting of fluid from the second housing. In some implementations, the fluid outlet end functions as a protrusion, wherein the protrusion has a diameter suitable for insertion into the interior of the bag connector housing. In some embodiments, an end of the bag connector is configured to insert into the interior of the second coupling element.

Disclosed herein, in certain embodiments, are second coupling elements that are spring-loaded (herein "spring-loaded coupling connector"). In some embodiments, the spring-loaded coupling connector comprises a) a second housing having a fluid inlet end and a fluid outlet end, wherein the fluid outlet end has a structure comprising one or more openings to allow for the exiting of fluid from the second housing and b) a second spring-loaded valve to regulate the exiting of fluid from the second housing; wherein depression of the second spring-loaded valve results in an open configuration to allow fluid to exit through the openings of the second housing; and wherein decompression of the second spring-loaded valve results in a closed configuration to restrict fluid from exiting the second housing.

In some embodiments, the second coupling element comprises a second spring element and a second moving door. In another embodiment, the spring-loaded valve further comprises a second spring seat or a second base. The second moving door may be made of a material comprising plastic, silicone, fluoropolymer, rubber, elastomer or any combination thereof. The second spring element may be made of a material comprising a metal or plastic. A metal spring includes, without limitation, magnetic resonance imaging compatible metals, including brass, steel, stainless steel, zinc coated steel, beryllium copper and bronze. An exemplary second spring element is a compression spring such as a helical compression spring. Examples of second spring elements include, without limitation, straight metal coil, concave (hourglass), conical and convex (barrel) springs. In some embodiments, the spring rate of the spring element is from about 0.009 N/mm (0.05 lbs/in) to about 2.63 N/mm (15 lbs/in), or preferably, from about 0.018 N/mm (0.1 lbs/in) to about 1.4 N/mm (8 lbs/in). In a preferred embodiment, in cases wherein a compression spring is used in both the first coupling element and a spring-loaded coupling connector, the spring rate of the first coupling element is different from the spring rate of the spring-loaded coupling connector. In some embodiments, the spring wire diameter is from about 0.254 mm (0.01 in) to about 1.27 mm (0.05 in). In one example, the maximum load of the compression spring is no more than 8 N, or preferably, no more than 5 N.

The second housing of the second coupling element may be constructed of any material suitable for containing fluid and/or matter. For example, the second housing is comprised of a plastic, including but not limited polyethylene, polypropylene, ABS, nylon, PET, and the like. In some embodiments, the fluid inlet end of the second housing has a wall of solid construction, so that fluid and/or matter within the interior of the fluid inlet end is not exposed to the external environment. In some embodiments, the fluid outlet end of the second housing has a plurality of openings in its structure. In some embodiments, the fluid outlet end of the second housing comprises at least 1, at least 2, at least 3, at least 4, at least 5, at least 10, at least 15 or at least 20 openings. In some embodiments, the fluid outlet end of the second housing comprises 1, 2, 3, 4, 5, 6, 7, 8, 9 or 10 openings. The openings may be of any size suitable to allow for the exiting of fluid and/or matter from the fluid outlet end. It is to be understood that the size of the openings may be smaller or larger depending on the components of the fluid and/or matter to be collected. For example, the fluid outlet end openings are smaller in a second coupling element suitable for use with a urinary catheter than the openings in a second coupling element suitable for use with a rectal catheter.

The second coupling element, in various embodiments, comprises an engaging element useful for coupling the second coupling element to a bag connector. In some embodiments, the engaging element of the second coupling element is a rotatable locking member having slots to receive one or more prongs from a bag connector for engagement to the bag connector in a twist lock-in mechanism; or vice versa. In another embodiment, a bag connector is engaged to the second coupling element in a coupled state by a snap-fit mechanism, wherein one of the coupling elements comprises at least one cantilever snap and the other coupling element comprises a ridge suitable for engaging with the one or more cantilever snaps.

In some embodiments, the second coupling element comprises a second housing having a fluid inlet end and a fluid outlet end, a sliding cover, a seal door, and at least one O-ring.

In some embodiments, the second housing comprises a tube attachment component to connect with a catheter or other medical grade tubing to receive fluid.

In some embodiments, the second coupling element has a component to connect to a bead strap for hanging.

In some embodiments, the second coupling element has an assembled length from about 40 mm to about 100 mm, from about 40 mm to about 90 mm, from about 50 mm to about 100 mm, from about 50 mm to about 90 mm, from about 60 mm to about 90 mm, or from about 70 mm to about 90 mm. In one example, the length of the second coupling element is about 70 mm, 71 mm, 72 mm, 73 mm, 74 mm, 75 mm, 76 mm, 77 mm, 78 mm, 79 mm, 80 mm, 81 mm, 82 mm, 83 mm, 84 mm, 85 mm, 86 mm, 87 mm, 88 mm, 89 mm or 90 mm. In one prototype, the second coupling element has a length of about 81.6 mm.

Medical Appliance with Bag Connector System

Disclosed herein, in certain embodiments, are medical appliances for the management of fecal or urinary waste. In some embodiments, the medical appliances comprise a catheter, a fluid collection container, and a bag connector system that connects the catheter to the fluid collection container. In some embodiments, the bag connector system comprises the fluid storage container. In some embodiments, the bag connector system comprises a first coupling element which comprises or attaches to a fluid storage container. In some embodiments, the bag connector system comprises the catheter. In some embodiments, the bag connector system comprises a second coupling element which comprises or attaches to a catheter. In further embodiments, a connection to the bag connector system is through the use of medical grade tubing. In other embodiments, the bag connector system is directly connected to the fluid storage container and/or to the catheter. In some embodiments, the medical grade tubing is draining tubing from the catheter. In some embodiments, the catheter is a rectal catheter. In other embodiments, the catheter is a urinary catheter.

In some embodiments, the bag connector system comprises a first coupling element comprising a housing having a fluid inlet portion and a fluid outlet portion, the first coupling element further comprising a spring-loaded valve to prevent fluid flow from exiting the fluid outlet portion; and a second coupling element comprising a second housing having a fluid inlet end and a fluid outlet end, the fluid outlet end configured to displace the spring-loaded valve of the first coupling element when inserted into the housing of the first coupling element. In some embodiments, the spring-loaded valve is positioned completely or partially within the housing of the first coupling element. In other or additional embodiments, the spring-loaded valve is positioned completely or partially outside of the housing of the first coupling element.

Disclosed herein, in certain embodiments, are medical appliances comprising a fluid collection or storage container and a bag connector system, the bag connector system comprising a first coupling element comprising a housing having a fluid inlet portion and a fluid outlet portion, the first coupling element further comprising a spring-loaded valve to prevent fluid flow from exiting the fluid outlet portion of the housing; and a second coupling element comprising a second housing having a fluid inlet end and a fluid outlet end, the fluid outlet end configured to displace the spring-loaded valve of the first coupling when inserted into the housing of the first coupling element; and wherein the fluid outlet portion of the first coupling element is connected to a fluid collection container and uncoupling of the first coupling element and the second coupling element results in minimal fluid contamination on the outer surfaces of the system. In some embodiments, the spring-loaded valve is positioned completely or partially within the housing of the first coupling element. In other or additional embodiments, the spring-loaded valve is positioned completely or partially outside of the housing of the first coupling element.

In some embodiments, each of the first coupling element and the second coupling element further comprises an engaging element to maintain the first coupling element and the second coupling element in a coupled state. In further embodiments, the first coupling element and the second coupling element are maintained in a coupled state by way of an interference fit mechanism, a twist lock-in (bayonet latch) mechanism, an annular snap-fit mechanism, a single cantilever snap-fit mechanism, and a multiple cantilever snap-fit mechanism comprising a plurality of cantilever snaps at the first coupling element which forms a snap-fit with a sliding cover of a second coupling element.

In some embodiments, the medical grade tubing is made of silicone, PVC, rubber, polyurethane, thermoplastic elastomer, or other suitable material. In various embodiments, the medical grade tubing can have an inner diameter of 0.30, 0.40, 0.50, 0.60, 0.70, 0.80, 0.90, 1, 2, 3, 4, 5, 6, 7, 8, 9, 10, 11, 12, 13, 14, 15, 16, 17, 18, 19, 20, 21, 22, 23, 24, 25 millimeters, or more, including increments therein.

Figure 4A:
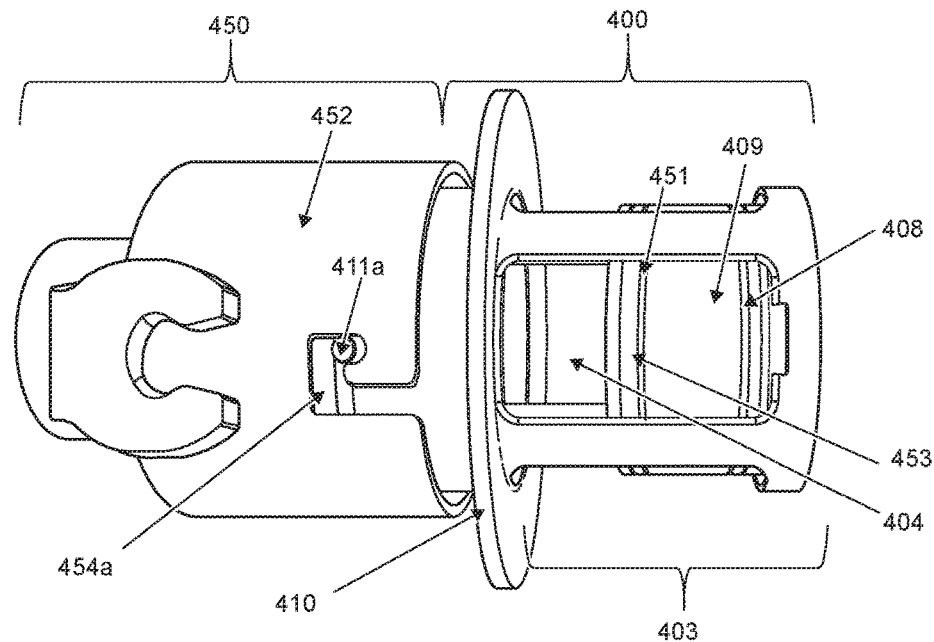
FIG. 4A provides a perspective view of an embodiment of a bag connector system comprising a spring-loaded bag connector coupled to a second coupling element.

An embodiment of a bag connector system is illustrated in FIG. 4a. In this embodiment, the bag connector system comprises a first coupling element 400 and a second coupling element 450 in a coupled state. The coupling of the two elements results in an open configuration of the first coupling element and an open configuration of the second coupling element. In this embodiment, the first coupling element is a spring-loaded bag connector, wherein the spring-loaded bag connector comprises a spring-loaded valve. As shown in FIG. 4a, the moving door 409 of the spring-loaded valve has been moved toward the bottom end of the first coupling element housing 401 by a fluid outlet end 451 of the second coupling element 450, compressing the spring of the first coupling element 408. In this embodiment, the fluid outlet end 451 of the second coupling element 450 pushes against the moving door 409 of the spring-loaded valve, eliminating the seal which was created and maintained by the spring-loaded valve mechanism during the uncoupled state. In this open configuration, fluid and/or matter within the housing of the second coupling element 452 can pass to the interior of the housing of the first coupling element 401, where the fluid and/or matter can then exit through the openings 404 of the fluid outlet portion 403 of the first coupling element housing to be collected in a fluid storage container (not shown). In this example, a fluid storage container may be connected to the first coupling element by a flange 410. The second coupling element 450 may further comprise one or more O-rings 453 that interacts with the interior of the first coupling element housing 401 during the coupling to create and maintain a seal between the coupling elements. The O-ring may be positioned around the outer surface of the housing of the second coupling element to interact with the inner surface of the housing of the first coupling element to create and maintain a seal. The O-ring may be made of silicone, rubber, fluoropolymer or another elastomer. In terms of shape, the O-ring may be a ring or a tapered ring.

Both the first coupling element 400 and the second coupling element 450 further comprise complementary components of an engaging or locking mechanism, which engages and/or maintains the first coupling element and the second coupling element in a coupled state. Such locking mechanisms include a twist lock-in mechanism, bayonet latch, or other locking mechanism which maintains a coupled state between the first coupling element and the second coupling element. For example, in some embodiments the external edge of the fluid inlet end of the second coupling element 450 comprises a rotatable locking member having at least one slot 454a which receives a prong 411a located on the outer surface of the fluid inlet portion 402 of the first coupling element. When the twist lock-in mechanism is in a first position, prongs 411a and 411b (not shown) can pass through complementary slots 454a and 454b, coupling or uncoupling the first coupling element 400 and the second coupling element 450. When the twist lock-in mechanism is in a second position, the prongs 411a and 411b (not shown) cannot pass through the complementary slots 454a and 454b, maintaining the first coupling element 400 and the second coupling element 450 in a coupled state. The twist lock-in mechanism is toggled between the first and second positions by rotating the coupled coupling elements in opposing directions along the axis of the fluid flow pathway. The prongs for use in a twist-lock mechanism can reside either in the first coupling element or in the second coupling element.

Figure 4B:
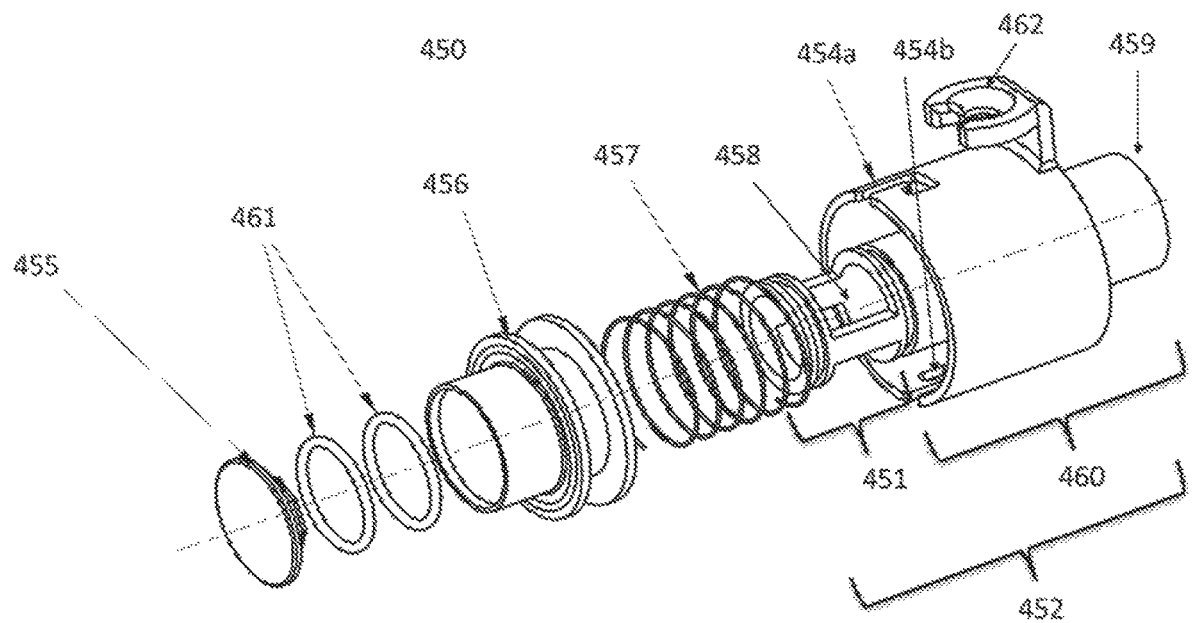
FIG. 4B provides an exploded view of an embodiment of a second coupling element which is a spring-loaded coupling connector.

FIG. 4b provides an exploded view of an embodiment of a second coupling element 450 as shown in the bag connector system of FIG. 4a. In this embodiment, the second coupling element is a spring-loaded coupling connector comprising a second housing 452 having a fluid inlet end 460 and a fluid outlet end 451. The exterior of the second housing 452 comprises a rotatable locking member 454 having slots 454a and 454b for engaging prongs of the first coupling element (e.g., prong 411a shown in FIG. 4a). The fluid inlet end comprises a tube attachment component to connect the second coupling element to a catheter or tubing for fluid collection, a catheter connector 459. The fluid outlet end 451 comprises a plurality of fluid outlet end openings 458 to allow for the passage of fluid from the interior of the second housing to the exterior of the second housing and through the housing of the bag connector. The second coupling element 450 further comprises a spring-loaded valve having a second moving door or seal door 455 and a second spring 457. The second coupling element 450 further comprises a sliding cover 456. The second coupling element 450 further comprises one or more O-rings 461. The second coupling element 450 further comprises a hanger 462 for holding an accessory element of a bag connector system. FIG. 4c provides a top view of the second coupling element of FIG. 4b, having a view of the seal door 455. FIG. 4d provides a cross-sectional view of the second coupling element of FIGS. 4a and 4b. The exterior of the fluid outlet portion 451 is at least partially covered with the sliding cover 456. The second spring 457 surrounds an internal portion of the fluid inlet end 460.

Figure 4E:
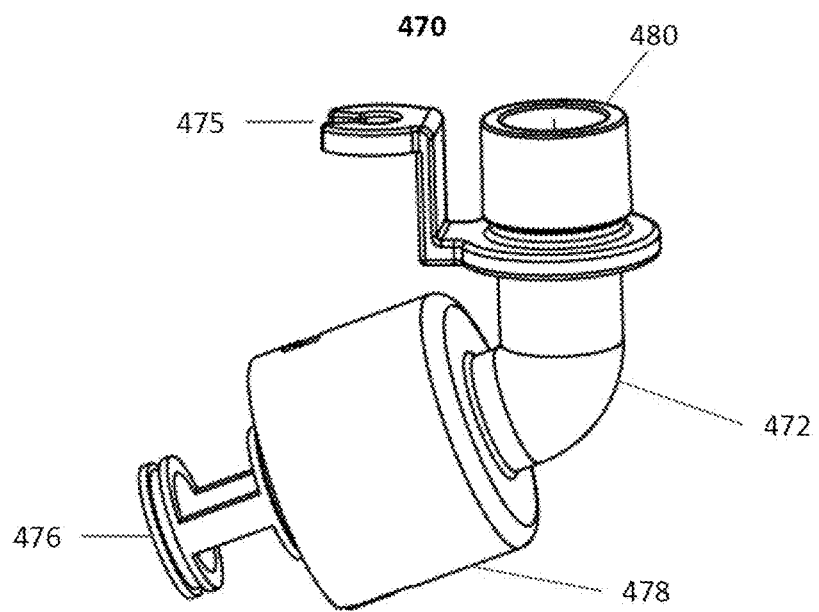
FIG. 4E provides a cross-sectional side view of another embodiment of the second coupling element with an almost 90 degree turn between the inlet and outlet.
Figure 4F:
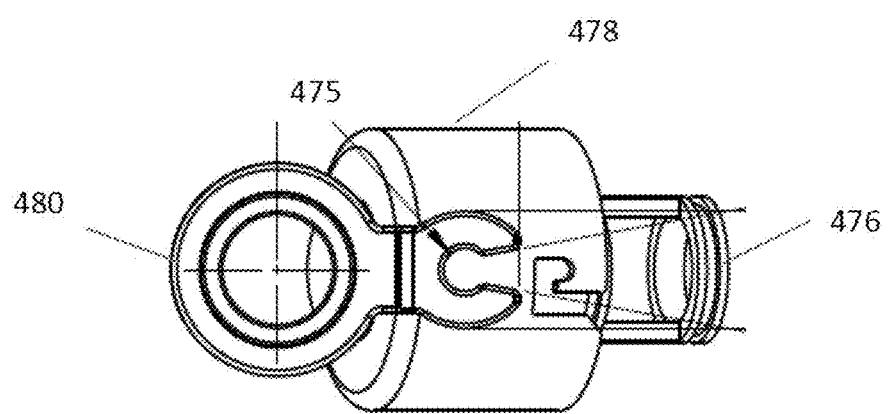
FIG. 4F provides a top view of the second coupling element of FIG. 4E

In other embodiments, the second coupling element may incorporate an angle in the connection to facilitate the flow from a catheter to a bag coupling, wherein the bag coupling is generally at a level below the bag at the end of a bed. FIGS. 4e and 4f depict side and top views of the second coupling element 470 incorporating a bend or elbow 472 in the fluid inlet for example, from the catheter connector 480 to the bag coupling unit via the second housing 478 and fluid outlet portion 476. The bend or elbow in the fluid inlet may comprise a bend of less than 140°, less than 130°, less than 120°, less than 110°, less than 100°, less than 90°, less than 80°, less than 70°, less than 60°, less than 50°, less than 45°, less than 40°, less than 35°, less than 30° or less than 25° relative to the housing 478. In other embodiments, the bend or elbow in the fluid inlet may comprise a bend of about 10° to about 140°, about 20° to about 120°, about 30° to about 120°, about 40° to about 120° or about 50° to about 120° relative to the housing 478. In other instances, the bend or elbow in the fluid inlet may comprise a bend of about 140°, about 135°, about 130°, about 135°, about 130°, about 125°, about 120°, about 115°, about 110°, about 105°, about 100°, about 95°, about 90°, about 85°, about 80°, about 75°, about 70°, about 65°, about 60°, about 55°, about 50° or about 45°, relative to the housing 478. The second coupling element 470 further comprises a hanger 475 for holding an accessory element of a bag connector system.

EXAMPLES

Example 1: Spring-Loaded Bag Connector

A spring-loaded bag connector was manufactured having the components shown in FIG. 1. The inner diameter of the entrance of the fluid inlet portion 102 of the bag connector is about 27.7 mm. The inner diameter of the fluid outlet portion 103 of the housing 101 is about 29.8 mm. The moving door 109 has an outer diameter of 29.5 mm and a rim height about 6.7 mm. The prongs 111 are each about 7.7 mm long and 3.1 mm in diameter, which is sufficient to provide enough strength for coupling the bag connector to a second coupling element. The seating element (or base) 105 has an outer diameter of about 34 mm and an opening of about 20.1 mm, wherein the seating element 105 supports the metal spring 108. The seating element 105 has 4 snap fit features 106 to allow it to be connected to the housing element. The housing 101, the moving door 109, and seating 105 are made by an injection molded process. Dow8007, a high density polyethylene (HDPE) with a density of 0.965 gm/cc3 made by Dow Chemical, was used as the material.

Example 2: Self-Closing Collection Bag and Use with Rectal Catheters

Figure 6:
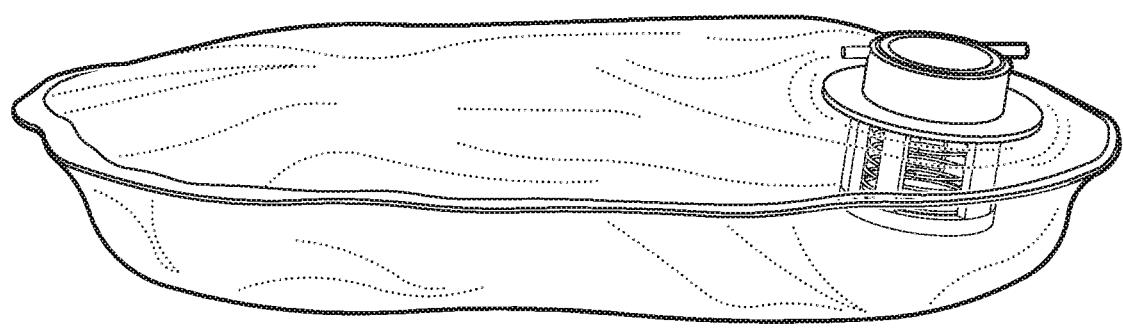
FIG. 6 provides a side view of an embodiment of an assembled collection bag comprising a spring-loaded bag connector in a closed configuration.

A self-closing collection bag, as shown in FIG. 6, comprises the spring-loaded bag connector from Example 1 and a collection bag. Panels of barrier film made from EVA/EVA/PVdC/EVA/EVA were heat welded to make into a collection bag. Optionally, a deodorizing filter is incorporated with the collection bag. In order to receive the protruded bag connector, the front panel of the collection bag may be thermoformed or blow-molded, forming a three-dimensional shape since a portion of the bag connector is recessed into the inside of the bag. Such a three-dimensional shape of the collection bag can increase the bag capacity without any change in the footprint (i.e., length and width) of the collection bag. The collection bag may optionally comprise folds or pleats, enabling a further increase in volume and capacity to the bag. The collection bag may also be rigid or semi-rigid in structure. The collection bag may also comprise additional support structures, including but not limited to supporting straps or fixtures to maintain the collection bag when filled. The front panel has a cut out so that the front panel of the collection bag can be welded onto the bag connector flange.

Figure 7:
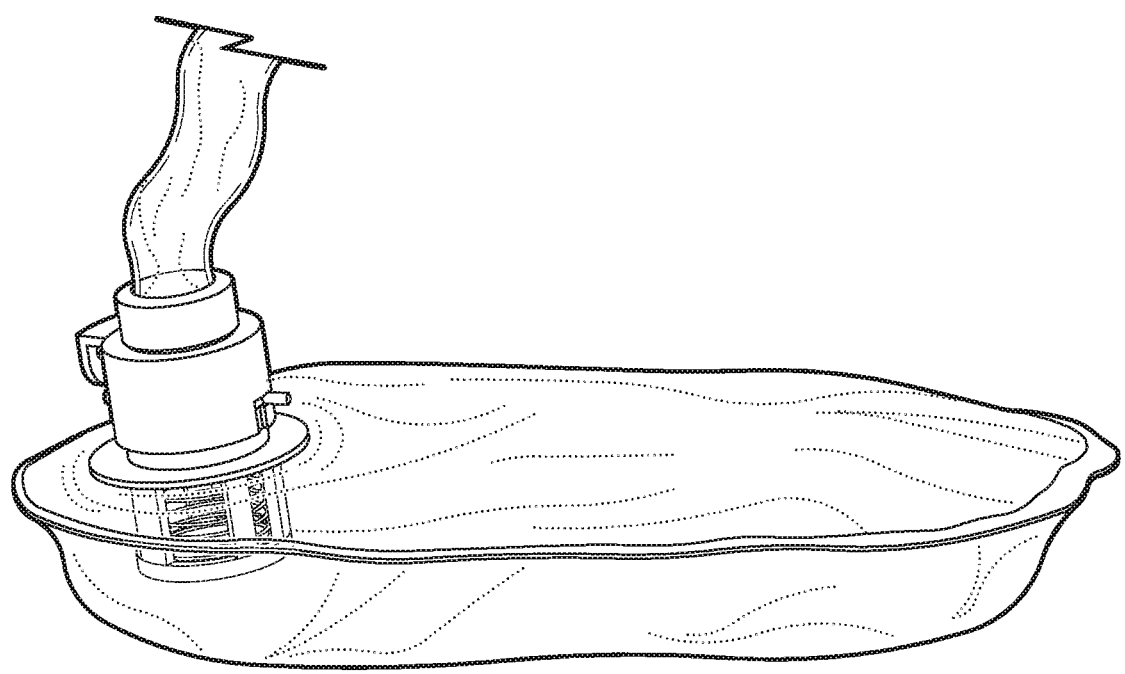
FIG. 7 provides a perspective view of an embodiment of an assembled collection bag coupled to the second coupling element with a catheter.

The self-closing collection bag, as shown in FIG. 6, is coupled to a second coupling element. The second coupling element is connected to a rectal catheter such as a catheter of the Flexi-Seal Fecal Management System or Signal Fecal Management System. The catheter is made from a silicone tube with a silicone retention balloon at one end, while the other end of the catheter is connected to the second coupling element. An example of a second coupling element useful to couple with the self-closing collection bag and a catheter is shown in FIG. 4. An example of a self-closing collection bag with the first spring-loaded bag connector coupled to a second coupling element which is then connected to a rectal catheter is shown in FIG. 7.

The collection bag is welded to the spring-loaded bag connector to form a disposal pouch system that can be connected to the catheter, through the second coupling element, when the catheter is in use. When the collection bag is full, the disposal pouch system is removed between the bag connector and the second coupling element so that another collection bag can be used.

Example 3: Bag Connector Systems and Use

A bag connector system comprising a first coupling element (in this example, the bag connector of Example 1) and a second coupling element was manufactured. The second coupling element was assembled from five components: a coupling housing, a sliding cover, a seal door (i.e., cap), and two O-rings. The coupling housing, the sliding cover, and the seal door (i.e., cap) were injection molded from the white pigmented acrylonitrile butadiene styrene (ABS). The seal door has an interference fitting to the sliding cover and can be sealed using an adhesive. The metal spring was selected in the same way as the metal spring in the first coupling element. Alternatively, a stronger metal spring may be selected in the second coupling element. The length of the second coupling element prototype is about 81 mm, having a feature to connect to a bead strap for hanging, and having an opening on the other side opposite to the bag connector coupling such that the second coupling element can be connected to a catheter to receive body waste. The second coupling element prototype has a diameter of about 27 mm, which is slightly smaller than the entrance of the bag connector prototype at about 27 mm.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A spring-loaded bag connector comprising a first coupling element and a second coupling element, the first coupling element comprising:
    a) a housing having a fluid inlet and a fluid outlet, wherein the fluid outlet has a structure comprising one or more openings to allow for the exiting of fluid from the housing when the first coupling element is in an open configuration; and
    b) a first spring-loaded valve comprising a seal door, a spring element, and a sliding cover; wherein the sliding cover is positioned around the one or more openings when the first coupling element is in a closed configuration to restrict fluid from exiting the housing through the one or more openings, and
    wherein the first coupling element transitions from the closed configuration to the open configuration upon coupling with a second coupling element to displace the sliding cover and permit fluid to exit the housing through the one or more openings, and the second coupling element comprises a second spring-loaded valve.

2. The bag connector of claim 1, wherein the first spring-loaded valve is self-closing upon uncoupling with the second coupling element, minimizing fluid contamination on exterior surfaces of the bag connector.

3. The bag connector of claim 1, further comprising an attachment fixture for attaching a fluid collection bag to the bag connector to generate a self-closing collection bag.

4. The self-closing collection bag of claim 3, wherein the fluid collection bag comprises a three-dimensional shape.

5. The self-closing collection bag of claim 4, wherein the fluid collection bag comprises pleats or folds.

6. The bag connector of claim 1, wherein the sliding cover is positioned around the housing of the first coupling element.

7. The bag connector of claim 1, comprising an engaging element for coupling the first coupling element to the second coupling element.

8. The bag connector of claim 7, wherein the first coupling element is bent at an angle of less than 140° relative to the housing.

9. The bag connector of claim 1, wherein the spring-loaded valve comprises an O-ring positioned between the housing and the sliding cover.

10. A medical appliance comprising a fluid collection container and a bag connector system, the bag connector system comprising:
    a) a first coupling element comprising: (a) a housing having a fluid inlet and a fluid outlet, wherein the fluid outlet has a structure comprising one or more openings, and (b) a first spring-loaded valve comprising a seal door, a spring element, and a sliding cover positionable around the open or more openings to restrict fluid from exiting the housing; and
    b) a second coupling element configured to displace the sliding cover and spring element upon coupling with the first coupling element;
    wherein the bag connector system is connectable to the fluid collection container whereby the one or more openings of the fluid outlet of the first coupling element is enclosed within the fluid collection container when the first coupling element and the second coupling element are coupled, and uncoupling of the first coupling element and the second coupling element results in minimal fluid contamination on an outer surface of the medical appliance, and
    wherein the second coupling element comprises a second spring-loaded valve, and the first coupling element is configured to displace the second spring-loaded valve; wherein displacement of the first spring-loaded valve results in the first coupling element having an open configuration and displacement of the second spring-loaded valve results in the second coupling element having an open configuration.

11. The medical appliance of claim 10, wherein displacement of the first spring-loaded valve results in the first coupling element having an open configuration allowing for fluid to exit the housing of the first coupling element via the one or more openings of the fluid outlet portion.

12. The medical appliance of claim 10, wherein the open configurations allow for fluid to flow between the second coupling element and the first coupling element and for fluid to exit from the first coupling element.

13. The medical appliance of claim 10, wherein the sliding cover is positioned around the housing of the first coupling element.

14. The medical appliance of claim 10, wherein each of the first coupling element and the second coupling element further comprise an engaging element to maintain the first coupling element and the second coupling element in a coupled state.

15. The medical appliance of claim 10, wherein the fluid collection container comprises a three-dimensional shape.

16. The medical appliance of claim 10, wherein the spring-loaded valve comprises an O-ring positioned between the housing and the sliding cover.

* * * * *

UNITED STATES PATENT AND TRADEMARK OFFICE
CERTIFICATE OF CORRECTION

PATENT NO. : 10,576,262 B2
APPLICATION NO. : 15/158426
DATED : March 3, 2020
INVENTOR(S) : Mingliang Lawrence Tsai et al.

Page 1 of 1

It is certified that error appears in the above-identified patent and that said Letters Patent is hereby corrected as shown below:

In the Claims

In Claim 10, at Column 26, Line 48:
Replace --open or more openings-- with --one or more openings--.

Signed and Sealed this
Twenty-sixth Day of May, 2020

Andrei Iancu
*Director of the United States Patent and Trademark Office*